United States Patent
Jones et al.

(10) Patent No.: US 10,913,060 B2
(45) Date of Patent: Feb. 9, 2021

(54) LOADING VIALS

(71) Applicant: BioFire Diagnostics, LLC, Salt Lake City, UT (US)

(72) Inventors: David E. Jones, Layton, UT (US); Kirk Max Ririe, Salt Lake City, UT (US); Stephanie Anne Thatcher, Salt Lake City, UT (US); Jarrett Avery Killpack, Salt Lake City, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 0 days.

(21) Appl. No.: 16/580,749

(22) Filed: Sep. 24, 2019

(65) Prior Publication Data
US 2020/0016589 A1 Jan. 16, 2020

Related U.S. Application Data

(63) Continuation of application No. 14/356,837, filed as application No. PCT/US2012/064286 on Nov. 9, 2012, now Pat. No. 10,464,060.
(Continued)

(51) Int. Cl.
*B01L 3/00* (2006.01)
*A61J 1/20* (2006.01)
(Continued)

(52) U.S. Cl.
CPC .............. *B01L 3/502* (2013.01); *A61J 1/1425* (2015.05); *A61J 1/20* (2013.01); *A61M 5/14228* (2013.01);
(Continued)

(58) Field of Classification Search
USPC .......................................................... 141/65
See application file for complete search history.

(56) References Cited

U.S. PATENT DOCUMENTS 2,953,132 A    9/1960  Richter et al.
3,493,503 A *  2/1970  Mass ...................... G01N 33/50
                                                        210/778
(Continued)

FOREIGN PATENT DOCUMENTS

CN    101501693    8/2009
EP    0634015      1/1995
(Continued)

OTHER PUBLICATIONS

Adler et al. "A real-time immuno-PCR assay for routine ultrasensitive quantification of proteins" Biochemical and Biophysical Research Communications, 308:240-250 (2003).
(Continued)

*Primary Examiner* — Timothy L Maust
*Assistant Examiner* — James R Hakomaki
(74) *Attorney, Agent, or Firm* — Myers Bigel, P.A.

(57) ABSTRACT

In one illustrative embodiment, a cannulated vial is provided, the cannulated vial comprising a vial body having a top surface at one end, a bottom surface at an opposite end, and exterior wall therebetween defining an interior vial volume, the top surface having an opening, a cannula extending from the bottom surface and having a first end, a second end and an outer surface therebetween defining a cannula volume, the first end in fluid communication with the interior vial volume, and a cap having a tongue, the tongue sized to sealably close the opening, the tongue further having a volume greater than or equal to the cannula volume.

20 Claims, 17 Drawing Sheets

Related U.S. Application Data

(60) Provisional application No. 61/558,113, filed on Nov. 10, 2011.

(51) Int. Cl.
  *A61J 1/14* (2006.01)
  *A61M 5/142* (2006.01)
  *B01L 7/00* (2006.01)

(52) U.S. Cl.
  CPC .............. *B01L 3/5082* (2013.01); *B01L 7/52* (2013.01); *B01L 2200/026* (2013.01); *B01L 2300/042* (2013.01); *B01L 2300/043* (2013.01); *B01L 2300/0838* (2013.01); *B01L 2300/0851* (2013.01); *B01L 2300/0858* (2013.01); *B01L 2300/0864* (2013.01); *B01L 2400/0406* (2013.01); *B01L 2400/049* (2013.01)

(56) References Cited

U.S. PATENT DOCUMENTS

| | | | |
|---|---|---|---|
| 4,303,071 A | | 12/1981 | Smith |
| 4,391,274 A | * | 7/1983 | Kagan ................... A61M 5/165 604/190 |
| 4,786,471 A | | 11/1988 | Jones et al. |
| 4,832,842 A | | 5/1989 | Limb |
| 5,005,721 A | * | 4/1991 | Jordan ................ B01L 3/50853 220/23.4 |
| 5,125,415 A | * | 6/1992 | Bell ..................... A61M 5/3145 215/DIG. 3 |
| 5,270,011 A | * | 12/1993 | Altherr ............... B01L 3/50825 215/216 |
| 5,429,803 A | | 7/1995 | Guirguis |
| 5,573,525 A | | 11/1996 | Watson et al. |
| 5,753,186 A | * | 5/1998 | Hanley ............... B01L 3/50825 422/512 |
| 5,942,191 A | | 8/1999 | Conway |
| 5,976,824 A | | 11/1999 | Gordon |
| 6,059,138 A | | 5/2000 | Labruyere |
| 6,146,895 A | | 11/2000 | Green et al. |
| 6,645,758 B1 | | 11/2003 | Schnipelsky et al. |
| 6,780,617 B2 | | 8/2004 | Chen |
| 7,029,465 B2 | * | 4/2006 | Heyes ..................... A61J 1/067 128/200.14 |
| 7,306,740 B2 | * | 12/2007 | Freund ............. A61B 17/32002 210/781 |
| 7,387,216 B1 | * | 6/2008 | Smith ................ B65D 47/0842 220/254.3 |
| 7,820,113 B2 | | 10/2010 | Myung et al. |
| 8,263,390 B2 | | 9/2012 | Tajima |
| 8,584,695 B2 | * | 11/2013 | Lau ....................... F16K 15/202 137/232 |
| 2002/0143298 A1 | * | 10/2002 | Marsden .................. G01N 1/14 604/190 |
| 2003/0042212 A1 | | 3/2003 | Steinel |
| 2004/0245163 A1 | | 12/2004 | Lim et al. |
| 2005/0064469 A1 | | 3/2005 | Schulz et al. |
| 2005/0075611 A1 | | 4/2005 | Hetzler et al. |
| 2005/0178216 A1 | | 8/2005 | Pitt et al. |
| 2006/0057738 A1 | | 3/2006 | Hall, Jr. |
| 2006/0153716 A1 | | 7/2006 | Shop et al. |
| 2006/0177354 A1 | | 8/2006 | Daf |
| 2007/0017914 A1 | * | 1/2007 | Shigesada ............ B01D 65/003 222/189.11 |
| 2009/0238725 A1 | | 9/2009 | Ellis et al. |
| 2010/0055383 A1 | | 3/2010 | Ririe et al. |
| 2010/0198392 A1 | | 8/2010 | Eliuk et al. |
| 2011/0004145 A1 | | 1/2011 | Beiriger et al. |
| 2011/0104026 A1 | | 5/2011 | Yoon et al. |
| 2011/0132109 A1 | | 6/2011 | Delaage |
| 2011/0301496 A1 | | 12/2011 | Lampropoulos et al. |
| 2011/0313143 A1 | | 12/2011 | Martin et al. |
| 2012/0294778 A1 | | 11/2012 | Daf |
| 2013/0109009 A1 | | 5/2013 | Kessel |
| 2014/0256058 A1 | | 9/2014 | Dobrowolski |

FOREIGN PATENT DOCUMENTS

| | | |
|---|---|---|
| EP | 0901822 | 3/1999 |
| GB | 2422795 | 8/2006 |
| WO | 9319368 | 9/1993 |

OTHER PUBLICATIONS

Adler et al. "Detection of Rotavirus from stool samples using a standardized immuno-PCR ("Imperacer") method with end-point and real-time detection" Biochemical and Biophysical Research Communications, 333:1289-1294 (2005).

Adler, Michael "Immuno-PCR as a Chemical Laboratory Tool" Advances in Clinical Chemistry, 39:239-292 (2005).

Allen et al. "An immuno-PCR method for detecting Bacillus thuringiensis Cry1Ac toxin" Journal of Immunological Methods, 308:109-115 (2006).

Barletta et al. "Lowering the Detection Limits of HIV-1 Viral Load Using Real-Time Immuo-PCR for HIV-1 p24 Antigen" Microbiology and Infectious Disease, 122:20-27 (2004).

Barletta et al. "Detection of ultra-low levels of pathologic prion protein in scrapie infected hamster brain homogenates using real-time immuno-PCR" Journal or Virological Methods, 127:154-164 (2005).

Chao et al. "A highly sensitive immuno-polymerase chain reaction assay for Clostridium botulinum neurotoxin type A" Toxicon, 43:27-34 (2004).

Elnifro et al. "Multiplex PCR: Optimization and Application in Diagnostic Virology" Clinical Microbiology Reviews 13(4):559-570 (2000).

Elniero et al. "Multiplex Polymerase Chain Reaction for Diagnosis of Viral and Chlamydial Keratoconjunctivities" Investigative Ophthalmology & Visual Science, 41:1816-1822 (2000).

Extended European Search Report corresponding to European Patent Application No. 12849369.9 (12 pages) (dated Oct. 27, 2015).

Giaever et al. "Genomic profiling of drug sensitivities via induced haploinsufficiency" Nature Genetics, 21:278-283 (1999).

Guncry et al. "Amplicon Melting Analysis with Labeled Primers: A Closed-Tube Method for Differentiating Homozygotes and Heterozygotes" Clinical Chemistry, 49(3):396-406 (2003).

Hendrickson et al. "High sensitivity multianalyte immunoassay using covalent DNA-labeled antibodies and polymerase chain reaction" Nucleic Acids Research, 23(3):522-529 (1995).

Hujer et al. "Analysis of Antibiotic Resistance Genes in Multidrug-Resistant *Acinetobacter* sp. Isolates from Military and Civilian Patients Treated at the Walter Reed Army Medical Center" Antimicrobial Agents and Chemotherapy, 50(12):4114-4123 (2006).

International Preliminary Report on Patentability corresponding to International Application No. PCT/US2012/084286 (8 pages) (May 13, 2014).

International Search Report and the Written Opinion of the International Searching Authority corresponding to International Application No. PCT/US2012/064286 (10 pages) (dated Feb. 5, 2013).

Joerger et al. "Analyte Detection with DNA-Labeled Antibodies and Polymerase Chain Reaction" Clinical Chemistry, 41(9):1371-1377 (1995).

Liang et al. "A highly sensitive immuno-PCR assay for detecting Group A *Streptococcus*" Journal of Immunological Methods, 279:101-110 (2003).

Lind et al. "Development and evaluation of three real-time immuno-PCR assemblages for quantification of PSA" Journal of Immunological Methods, 304:107-116 (2005).

McKie et al. "A quantitative immuno-PCR assay for the detection of mumps-specific IgG" Journal of Immunological Methods, 270:135-141 (2002).

Niemeyer et al. "Immuno-PCR: high sensitivity detection of proteins by nucleic acid amplification" Trends in Biotechnology, 23(4):208-216 (2005).

(56) References Cited

OTHER PUBLICATIONS

Partial Supplementary European Search Report corresponding to European Patent Application No. 12849369.9 (7 pages) (Jul. 6, 2015).

Sanchez et al. "A multiplex assay with 52 single nucleotide polymorphisms for human identification" Electrophoresis, 27:1713-1724 (2006).

Sano et al. "Immuno-PCR: Very Sensitive Antigen Detection by Means of Specific Antibody-DNA Conjugates" Science, 258(5079):120-122 (1992).

Schiavo et al. "Comparison of Fluorometric Detection Methods for Quantitative Polymerase Chain Reaction (PCR)" Journal of Immunoassay & Immunochemistry, 26:1-12 (2005).

Winzeler et al. "Functional Characterization of the *S. cerevisiae* Genome by Gene Deletion and Parallel Analysis" Science, 285:901-906 (1999).

Wittwer et al. "Minimizing the Time Required for DNA Amplification by Efficient Heat Transfer to Small Samples" Analytical Biochemistry, 186:328-331 (1990).

Wittwer et al. "Rapid Cycle DNA Amplification: Time and Temperature Optimization" BioTechniques, 10(1):76-83 (1991).

Wittwer et al. "Continuous Fluorescence Monitoring of Rapid Cycle DNA Amplification" BioTechniques, 22:130-138 (1997).

Wittwer et al. "The LightCycler: A Microvolume Multisample Fluorimeter with Rapid Temperature Control" BioTechniques, 22(1):176-181 (1997).

Wittwer et al. "High-Resolution Genotyping by Amplicon Melting Analysis Using LCGreen" Clinical Chemistry, 49(6):853-860 (2003).

Wu et al. "Detection of Clostridium botulinum neurotoxin type A using immuno-PCR" Letters in Applied Microbiology, 32:321-325 (2001).

Zhou et al. "Closed-Tube Genotyping with Unlabeled Oligonucleotide Probes and a Saturating DNA Dye" Clinical Chemistry, 50(8):1328-1335 (2004).

\* cited by examiner

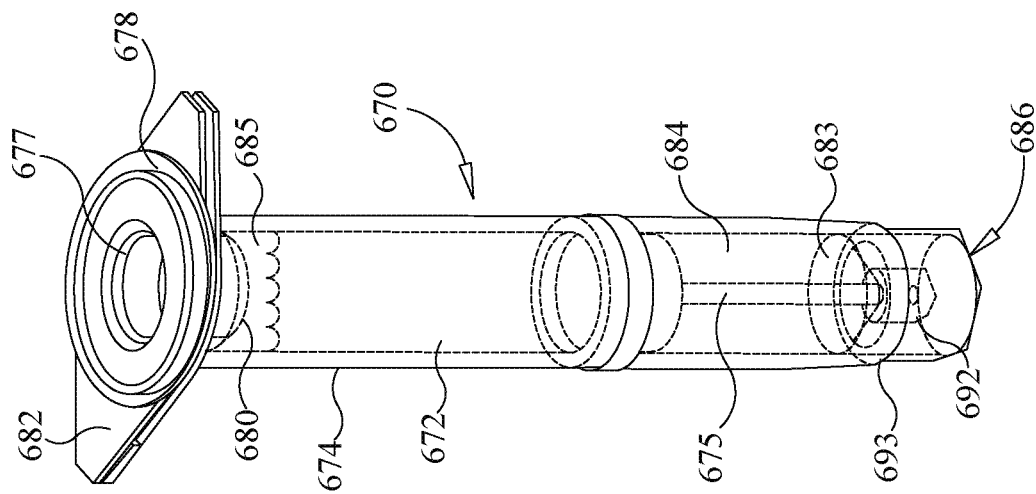
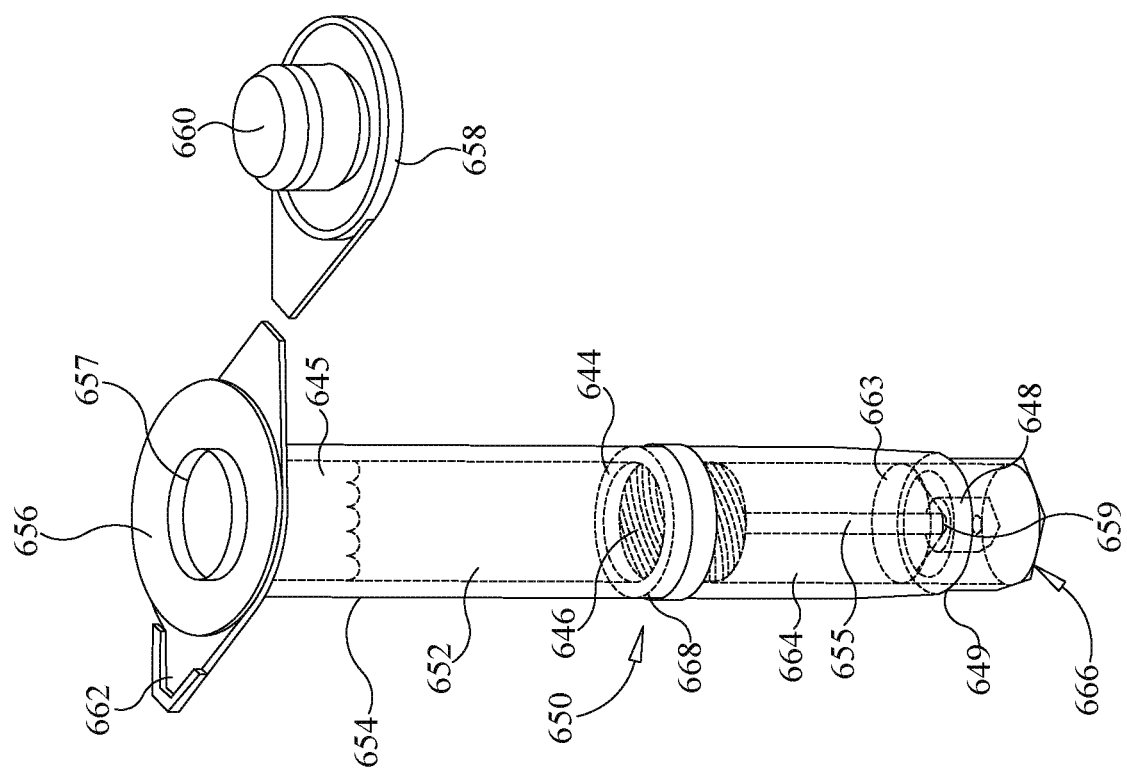
FIG. 18
FIG. 17

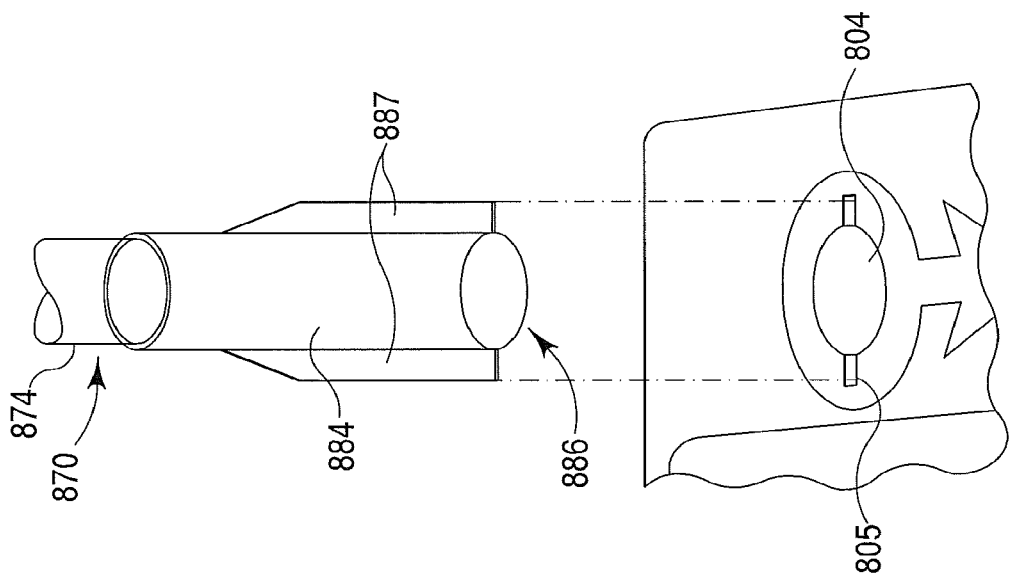
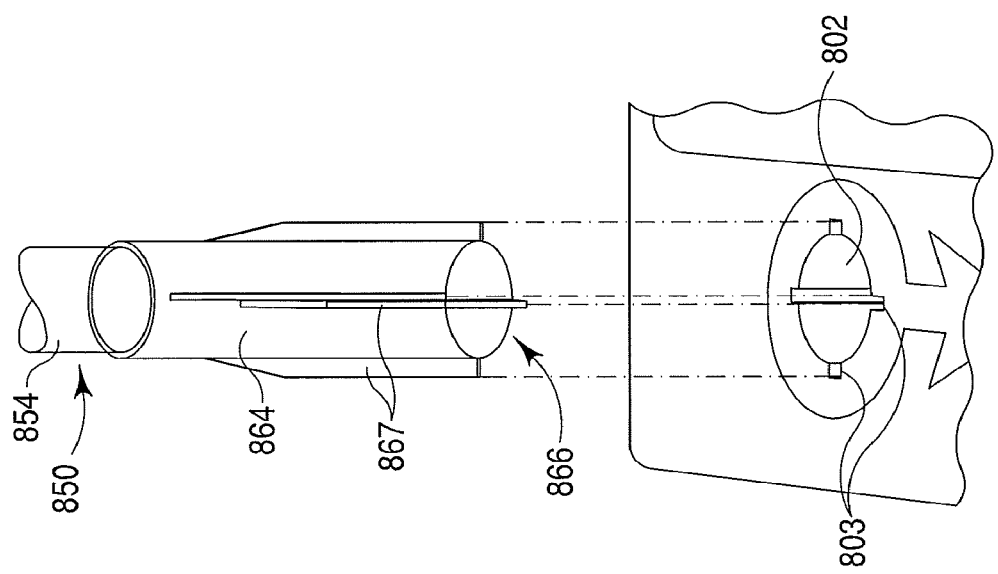

LOADING VIALS

STATEMENT OF PRIORITY

This application is a continuation application of U.S. patent application Ser. No. 14/356,837, filed May 7, 2014, which is a 35 USC § 371 national phase application of International Application Serial No. PCT/US2012/064286, filed Nov. 9, 2012, which claims the benefit under 35 U.S.C. § 119(e) of U.S. Provisional Application No. 61/558,113, filed Nov. 10, 2011, the entire contents of each of which are incorporated by reference herein.

BACKGROUND OF THE INVENTION

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. However, this further handling can be expensive and may lead to contamination or other problems.

The present invention addresses various issues of handling materials to perform biological analysis.

SUMMARY OF THE INVENTION

In one illustrative embodiment, a cannulated vial is provided, the cannulated vial comprising a vial body having a top surface at one end, a bottom surface at an opposite end, and exterior wall therebetween defining an interior vial volume, the top surface having an opening, a cannula extending from the bottom surface and having a first end, a second end and an outer surface therebetween defining a cannula volume, the first end in fluid communication with the interior vial volume, and a cap having a tongue, the tongue sized to sealably close the opening, the tongue further having a volume greater than or equal to the cannula volume. Illustratively, placing the tongue into the opening of the top surface to sealably close the opening pressurizes the interior vial volume, and removal of the bottom cap causes pressurized fluid to be forced into the cannula. A filter may be located near the bottom surface of the vial body, the filter configured to filter fluid as the fluid passes into the cannula. In one embodiment, the filter has a pore size large enough to allow protozoans or other microbes to pass, but small enough to capture larger particulate matter. A second vial may be provided to provide hydration fluid to the fluidic system.

In another illustrative embodiment, a cannulated vial is provided, the cannulated vial comprising a vial body having an interior vial volume that is sealed from an outside environment by one or more external walls, a cannula extending from a bottom surface of the vial body and having a first end and a second end connected by an outer surface and defining an interior cannula volume, the first end in fluid communication with the interior vial volume, a removable bottom cap having first end sized and shaped to removably seal the second end of the cannula from the outside environment when the bottom cap is affixed to the second end of the cannula, wherein fluid provided in the interior volume is under pressure, and removal of the bottom cap exposes the second end of the cannula to the outside environment, thereby forcing fluid through the cannula.

In yet another illustrative embodiment, a pouch loading station is provided, the pouch loading station comprising a slot configured for receiving the pouch, one or more receptacles, each receptacle configured to receive a cannulated vial, each cannulated vial comprising a vial body configured for sealing an interior volume from an outside environment, a cannula extending from a bottom surface of the vial body and having a first end and a second end, the first end in fluid communication with the interior volume, a removable bottom cap sealing the second end of the cannula from the outside environment, wherein each receptacle is shaped for mating with a shape of its respective bottom cap, to aid removal of the bottom cap. If more than one receptacle is provided, the receptacles may be sized or shaped differently to receive differently sized or shaped bottom caps.

In still another embodiment, a method is provided for loading a fluidic system, comprising providing a cannulated vial, the cannulated vial comprising a vial body having an interior volume sealed from an outside environment, the interior volume comprising a fluid and a volume of gas provided under pressure, a cannula extending from a bottom surface of the vial body and having a first end and a second end, the first end in fluid communication with the interior volume, and the second end of the cannula sealed from the outside environment, unsealing the second end of the cannula, whereby pressure in the vial body forces fluid into the cannula, placing the second end into the fluidic system, whereby the fluidic system is provided under vacuum, and allowing the vacuum to draw fluid from the cannulated vial, wherein the fluid is also driven through the cannula and into the fluidic system by expansion of the gas in the vial body.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 17 shows a loading vial for loading a sample into the pouch of FIG. 12.

FIG. 18 shows a hydration vial for providing a hydration fluid to the pouch of FIG. 12.

FIG. 20 shows a portion of the sample vial of FIG. 19 and how the sample vial keys to the sample vial receptacle of loading station of FIG. 19.

FIG. 21 shows a portion of a hydration vial of FIG. 19 and how the hydration vial keys to the hydration vial receptacle of loading station of FIG. 19.

DETAILED DESCRIPTION

The self-contained nucleic acid analysis pouches described herein may be used to assay a sample for the presence of various biological substances, illustratively antigens and nucleic acid sequences, illustratively in a single closed system. In one embodiment, the pouch is used to assay for multiple pathogens. Illustratively, various steps may be performed in the optionally disposable pouch, including nucleic acid preparation, primary large volume multiplex PCR, dilution of primary amplification product, and secondary PCR, culminating with real-time detection and/or post-amplification analysis such as melting-curve analysis. It is understood, however, that pathogen detection is one exemplary use and the pouches may be used for other nucleic acid analysis or detection of other substances, including but not limited to peptides, toxins, and small molecules. Further, it is understood that while the various steps may be performed in pouches of the present invention, one or more of the steps may be omitted for certain uses, and the pouch configuration may be altered accordingly.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. It is understood that protocols may need to be adjusted accordingly.

Figure 1:
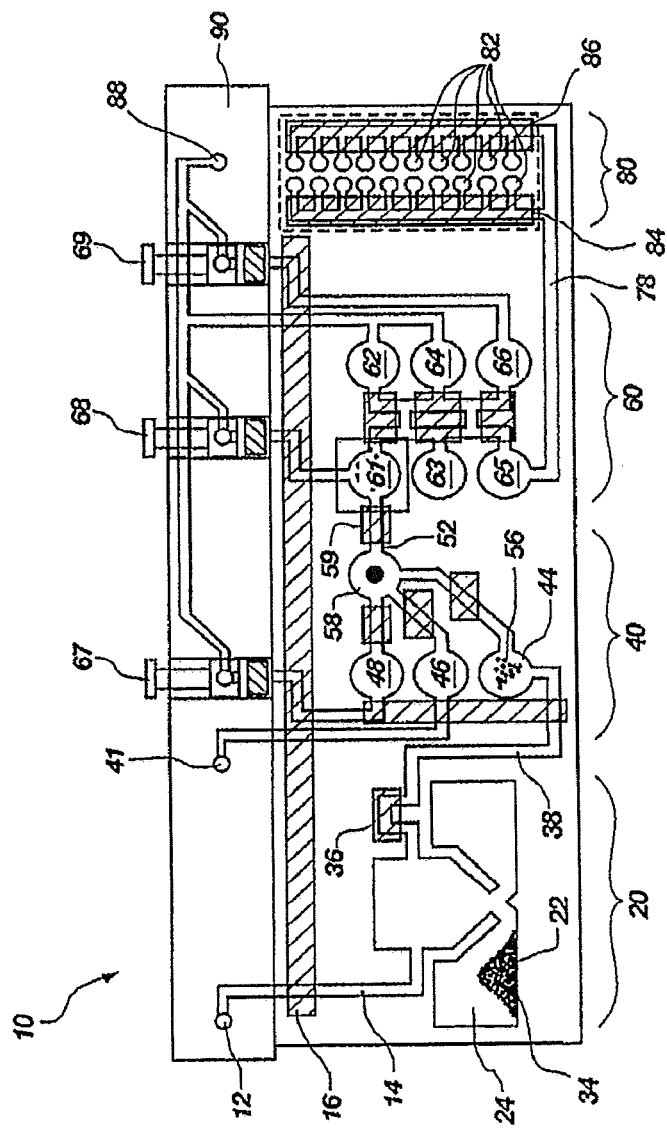
FIG. 1 shows a flexible pouch according to one embodiment of this invention.

FIG. 1 shows an illustrative self-contained nucleic acid analysis pouch 10. Pouch 10 has a cell lysis zone 20, a nucleic acid preparation zone 40, a first-stage amplification zone 60, and a second-stage amplification zone 80. A sample containing nucleic acid is introduced into the pouch 10 via sample injection port 12. Pouch 10 comprises a variety of channels and blisters of various sizes and is arranged such that the sample flows through the system. The sample passes through the various zones and is processed accordingly.

Sample processing occurs in various blisters located within pouch 10. Various channels are provided to move the sample within and between processing zones, while other channels are provided to deliver fluids and reagents to the sample or to remove such fluids and reagents from the sample. Liquid within pouch 10 illustratively is moved between blisters by pressure, illustratively pneumatic pressure, as described below, although other methods of moving material within the pouch are contemplated.

While other containers may be used, illustratively, pouch 10 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and Channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by trying different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in the blisters 82 of the second stage amplification zone 80 of pouch 10, then one or both layers at blisters 82 would be left without the foil. In the example of PCR, film laminates composed of polyester (Mylar, Dupont, Wilmington Del.) of about 0.0048 inch (0.1219 mm) thick and polypropylene films of 0.001-0.003 inch (0.025-0.076 mm) thick perform well. Illustratively, pouch 10 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pneumatic pressure, the pouch material illustratively is flexible enough to allow the pneumatic pressure to have the desired effect. The term "flexible" is herein used to describe a physical characteristic of the material of pouch. The term "flexible" is herein defined as readily deformable by the levels of pneumatic pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 10 may be made of a rigid material or may be reinforced with a rigid material.

Illustratively, a plastic film is used for pouch 10. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 10 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components. This separate spotting is discussed further below, with respect to FIG. 5*b*, but it is understood that such spotting may be used with any of the embodiments discussed herein.

Figure 2:
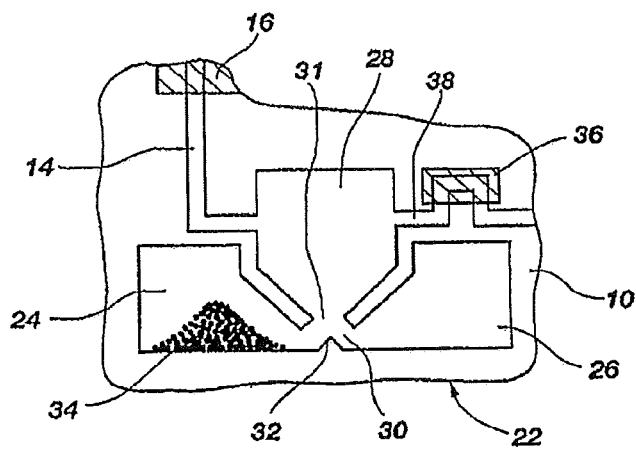
FIG. 2 shows an embodiment of the cell lysis zone of the flexible pouch according to FIG. 1.
Figure 2A:
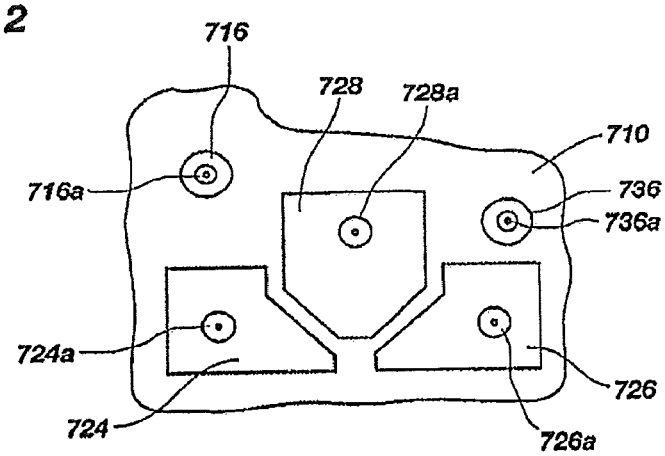
FIG. 2a shows an embodiment of a portion of a bladder corresponding to the cell lysis zone shown in FIG. 2.

When pneumatic pressure is used to move materials within pouch 10, in one embodiment a "bladder" may be employed. The bladder assembly 710, a portion of which is shown in FIG. 2*a*, may be manufactured in a process similar to that of making the pouch, but individual blisters in the bladder assembly 710 include pneumatic fittings (illustratively fitting 724*a*) allowing individual bladders within the bladder assembly 710 to be pressurized by a compressed gas source. Because the bladder assembly is subjected to compressed gas and may be used multiple times, the bladder assembly may be made from tougher or thicker material than the pouch. Alternatively, bladders may be formed from a series of plates fastened together with gaskets, seals, valves, and pistons. Other arrangements are within the scope of this invention.

When pouch 10 is placed within the instrument, the pneumatic bladder assembly 710 is pressed against one face of the pouch 10, so that if a particular bladder is inflated, the pressure will force the liquid out of the corresponding blister in the pouch 10. In addition to pneumatic bladders corresponding to many of the blisters of pouch 10, the bladder assembly may have additional pneumatic actuators, such as bladders or pneumatically-driven pistons, corresponding to various channels of pouch 10. When activated, these additional pneumatic actuators form pinch valves to pinch off and close the corresponding channels. To confine liquid within a particular blister of pouch 10, the pinch valve pneumatic actuators are inflated over the channels leading to and from the blister, such that the actuators function as pinch valves to pinch the channels shut. Illustratively, to mix two volumes of liquid in different blisters, the pinch valve pneumatic actuator sealing the connecting channel is depressurized, and the pneumatic bladders over the blisters are alternately pressurized, forcing the liquid back and forth through the channel connecting the blisters to mix the liquid therein. The pinch valve pneumatic actuators may be of various shapes and sizes and may be configured to pinch off more than one channel at a time. Such an illustrative pinch valve is illustrated in FIG. 1 as pinch valve 16, which may be used to close all injection ports. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch could be transitioned in one or two dimensions such that a small number of actuators could be used for several of the processing stations including sample disruption, nucleic-acid capture, first and second-stage PCR, and other applications of the pouch such as immunoassay and immuno-PCR. Rollers acting on channels and blisters could prove particularly useful in a configuration in which the pouch is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

With reference to FIG. 1, an illustrative sample pouch 10 configured for nucleic acid extraction and multiplex PCR is provided. The sample enters pouch 10 via sample injection port 12 in fitment 90. Injection port 12 may be a frangible seal, a one-way valve, or other entry port. Vacuum from inside pouch 10 may be used to draw the sample into pouch 10, a syringe or other pressure may be used to force the sample into pouch 10, or other means of introducing the sample into pouch 10 via injector port 12 may be used. The sample travels via channel 14 to the three-lobed blister 22 of the cell lysis zone 20, wherein cells in the sample are lysed. Once the sample enters three-lobed blister 22, pinch valve 16 is closed. Along with pinch valve 36, which may have been already closed, the closure of pinch valve 16 seals the sample in three-lobed blister 22. It is understood that cell lysis may not be necessary with every sample. For such samples, the cell lysis zone may be omitted or the sample may be moved directly to the next zone. However, with many samples, cell lysis is needed. In one embodiment, bead-milling is used to lyse the cells.

Bead-milling, by shaking or vortexing the sample in the presence of lysing particles such as zirconium silicate (ZS) beads 34, is an effective method to form a lysate. It is understood that, as used herein, terms such as "lyse," "lysing," and "lysate" are not limited to rupturing cells, but that such terms include disruption of non-cellular particles, such as viruses. FIG. 2 displays one embodiment of a cell lysis zone 20, where convergent flow creates high velocity bead impacts, to create lysate. Illustratively, the two lower lobes 24, 26 of three-lobed blister 22 are connected via channel 30, and the upper lobe 28 is connected to the lower lobes 24, 26 at the opposing side 31 of channel 30. FIG. 2a shows a counterpart portion of the bladder assembly 710 that would be in contact with the cell lysis zone 20 of the pouch 10. When pouch 10 is placed in an instrument, adjacent each lobe 24, 26, 28 on pouch 10 is a corresponding pneumatic bladder 724, 726, 728 in the bladder assembly 710. It is understood that the term "adjacent," when referring to the relationship between a blister or channel in a pouch and its corresponding pneumatic actuator, refers to the relationship between the blister or channel and the corresponding pneumatic actuator when the pouch is placed into the instrument. In one embodiment, the pneumatic fittings 724a, 726a of the two lower pneumatic bladders 724, 726 adjacent lower lobes 24, 26 are plumbed together. The pneumatic fittings 724a, 726a and the pneumatic fitting 728a of upper pneumatic bladder 728 adjacent upper lobe 28 are plumbed to the opposing side of an electrically actuated valve configured to drive a double-acting pneumatic cylinder. Thus configured, pressure is alternated between the upper pneumatic bladder 728 and the two lower pneumatic bladders 724, 726. When the valve is switched back and forth, liquid in pouch 10 is driven between the lower lobes 24, 26 and the upper lobe 28 through a narrow nexus 32 in channel 30. As the two lower lobes 24, 26 are pressurized at the same time, the flow converges and shoots into the upper lobe 28. Depending on the geometry of the lobes, the collision velocity of beads 34 at the nexus 32 may be at least about 12 m/sec, providing high-impact collisions resulting in lysis. The illustrative three-lobed system allows for good cell disruption and structural robustness, while minimizing size and pneumatic gas consumption. While ZS beads are used as the lysing particles, it is understood that this choice is illustrative only, and that other materials and particles of other shapes may be used. It is also understood that other configurations for cell lysis zone 20 are within the scope of this invention.

While a three-lobed blister is used for cell lysis, it is understood that other multi-lobed configurations are within the scope of this invention. For instance, a four-lobed blister, illustratively in a cloverleaf pattern, could be used, wherein the opposite blisters are pressurized at the same time, forcing the lysing particles toward each other, and then angling off to the other two lobes, which then may be pressurized together. Such a four-lobed blister would have the advantage of having high-velocity impacts in both directions. Further, it is contemplated that single-lobed blisters may be used, wherein the lysing particles are moved rapidly from one portion of the single-lobed blister to the other. For example, pneumatic actuators may be used to close off areas of the single-lobed blister, temporarily forming a multi-lobed blister in the remaining areas. Other actuation methods may also be used such as motor, pneumatic, hydraulic, or electromagnetically-driven paddles acting on the lobes of the device. Rollers or rotary paddles can be used to drive fluid together at the nexus 32 of FIG. 2, illustratively if a recirculation means is provided between the upper and lower lobes and the actuator provides peristaltic pumping action. Other configurations are within the scope of this invention.

Figure 2B:
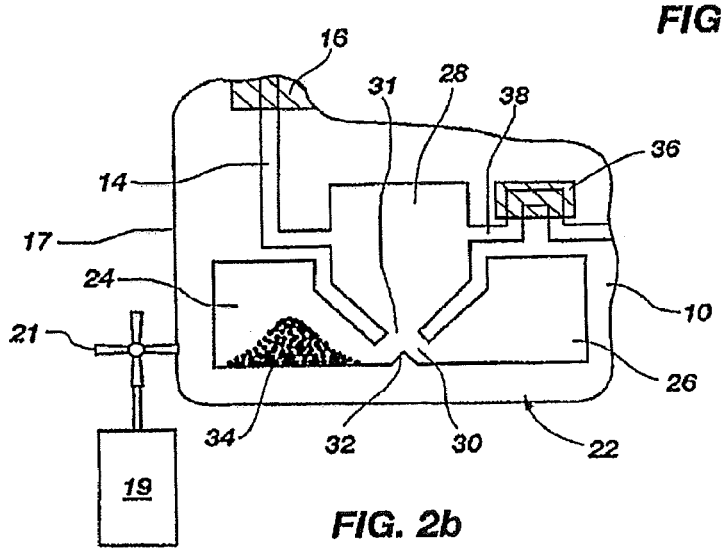
FIG. 2b shows an embodiment of the cell lysis zone of the flexible pouch according to FIG. 1 having an alternative vortexing mechanism.
Figure 12:
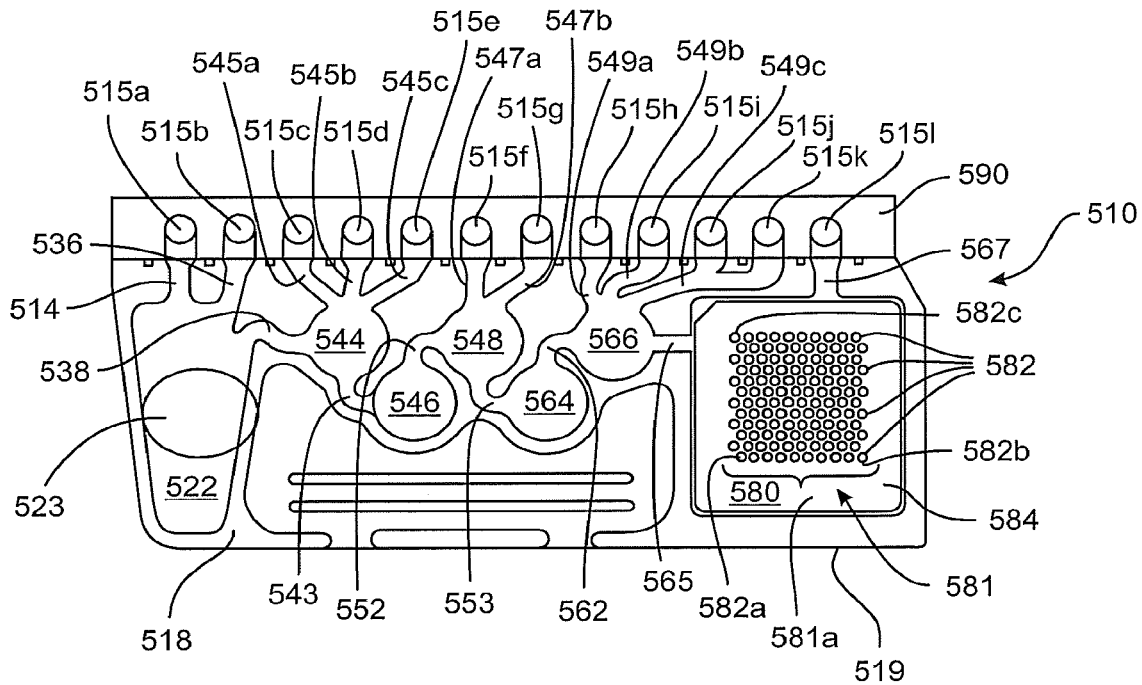
FIG. 12 is similar to FIG. 6, except showing a pouch having a second-stage high density array.
Figure 13:
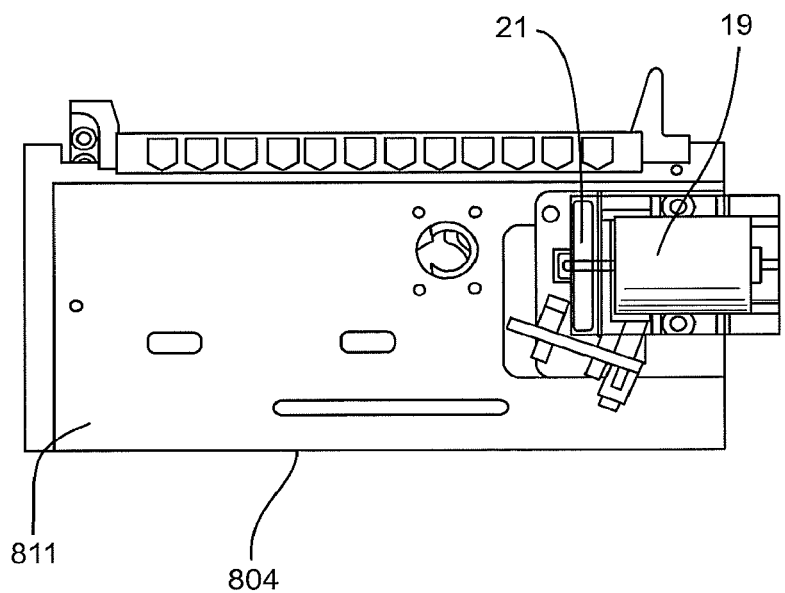
FIG. 13 shows a modification of a component of the instrument of FIG. 8. A support member has been provided with a motor configured for use with the pouch of FIG. 12.

It may also be possible to move the sample and lysing particles quickly enough to effect lysis within a single-lobed lysis blister without temporarily forming a multi-lobed blister. In one such alternative embodiment, as shown in FIG. 2b, vortexing may be achieved by impacting the pouch with rotating blades or paddles 21 attached to an electric motor 19. The blades 21 may impact the pouch at the lysis blister or may impact the pouch near the lysis blister, illustratively at an edge 17 adjacent the lysis blister. In such an embodiment, the lysis blister may comprise one or more blisters. FIG. 12 shows an embodiment comprising one such lysis blister 522. FIG. 13 shows a bead beating motor 19, comprising blades 21, that may be mounted on a first side 811 of second support member 804, of instrument 800 shown in FIG. 8. It is understood, however, that motor 19 may be mounted on first support member 802 or on other structure of instrument 800.

FIG. 2a also shows pneumatic bladder 716 with pneumatic fitting 716a, and pneumatic bladder 736 with pneumatic fitting 736a. When the pouch 10 is placed in contact with bladder assembly 710, bladder 716 lines up with channel 12 to complete pinch valve 16. Similarly, bladder 736 lines up with channel 38 to complete pinch valve 36. Operation of pneumatic bladders 716 and 736 allow pinch valves 16 and 36 to be opened and closed. While only the portion of bladder assembly 710 adjacent the cell lysis zone is shown, it is understood that bladder assembly 710 would be provided with similar arrangements of pneumatic blisters to control the movement of fluids throughout the remaining zones of pouch 10.

Other prior art instruments teach PCR within a sealed flexible container. See, e.g., U.S. Pat. Nos. 6,645,758 and 6,780,617, and co-pending U.S. patent application Ser. No. 10/478,453, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

Figure 3:
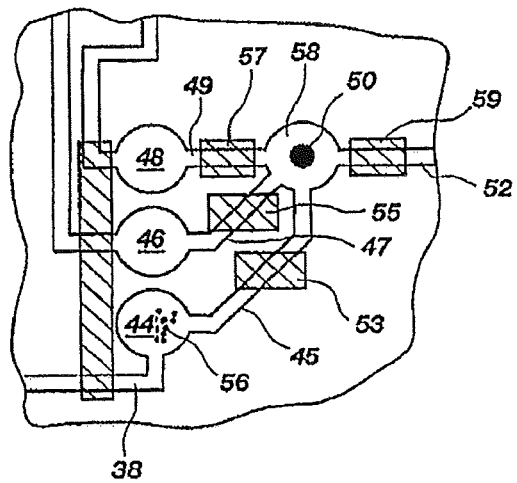
FIG. 3 shows an embodiment of the nucleic acid preparation zone of the flexible pouch according to FIG. 1.

Once the cells are lysed, pinch valve 36 is opened and the lysate is moved through channel 38 to the nucleic acid preparation zone 40, as best seen in FIG. 3, after which, pinch valve 36 is closed, sealing the sample in nucleic acid preparation zone 40. In the embodiment illustrated in FIG. 3, purification of nucleic acids takes the bead-milled material and uses affinity binding to silica-based magnetic-beads 56, washing the beads with ethanol, and eluting the nucleic acids with water or other fluid, to purify the nucleic acid from the cell lysate. The individual components needed for nucleic acid extraction illustratively reside in blisters 44, 46, 48, which are connected by channels 45, 47, 49 to allow reagent mixing. The lysate enters blister 44 from channel 38. Blister 44 may be provided with magnetic beads 56 and a suitable binding buffer, illustratively a high-salt buffer such as that of 1-2-3™ Sample Preparation Kit (Idaho Technology, Salt Lake City, Utah) or either or both of these components may be provided subsequently through one or more channels connected to blister 44. The nucleic acids are captured on beads 56, pinch valve 53 is then opened, and the lysate and beads 56 may be mixed by gentle pressure alternately on blisters 44 and 58 and then moved to blister 58 via pneumatic pressure illustratively provided by a corresponding pneumatic bladder on bladder assembly 710. The magnetic beads 56 are captured in blister 58 by a retractable magnet 50, which is located in the instrument adjacent blister 58, and waste may be moved to a waste reservoir or may be returned to blister 44 by applying pressure to blister 58. Pinch valve 53 is then closed. The magnetic beads 56 are washed with ethanol, isopropanol, or other organic or inorganic wash solution provided from blister 46, upon release of pinch valve 55. Optionally, magnet 50 may be retracted allowing the beads to be washed by providing alternate pressure on blisters 46 and 58. The beads 56 are once again captured in blister 58 by magnet 50, and the non-nucleic acid portion of the lysate is washed from the beads 56 and may be moved back to blister 46 and secured by pinch valve 55 or may be washed away via another channel to a waste reservoir. Once the magnetic beads are washed, pinch valve 57 is opened, releasing water (illustratively buffered water) or another nucleic acid eluant from blister 48. Once again, the magnet 50 may be retracted to allow maximum mixing of water and beads 56, illustratively by providing alternate pressure on blisters 48 and 58. The magnet 50 is once again deployed to collect beads 56. Pinch valve 59 is released and the eluted nucleic acid is moved via channel 52 to first-stage amplification zone 60. Pinch valve 59 is then closed, thus securing the sample in first-stage amplification zone 60.

It is understood that the configuration for the nucleic acid preparation zone 40, as shown in FIG. 3 and described above, is illustrative only, and that various other configurations are possible within the scope of the present disclosure.

The ethanol, water, and other fluids used herein may be provided to the blisters in various ways. The fluids may be stored in the blisters, the necks of which may be pinched off by various pinch valves or frangible portions that may be opened at the proper time in the sample preparation sequence. Alternatively, fluid may be stored in reservoirs in the pouch as shown pouch 110 in FIG. 5, or in the fitment as discussed with respect to pouch 210 of FIG. 6, and moved via channels, as necessary. In still another embodiment, the fluids may be introduced from an external source, as shown in FIG. 1, especially with respect to ethanol injection ports 41, 88 and plungers 67, 68, 69. Illustratively, plungers 67, 68, 69 may inserted into fitment 90, illustratively of a more rigid material, and may provide a measured volume of fluid upon activation of the plunger, as in U.S. patent application Ser. No. 10/512,255, herein incorporated by reference. Alternatively, plunger may be a softer material and the fitment may be the more rigid material. The measured volume may be the same or different for each of the plungers. Finally, in yet another embodiment, the pouch may be provided with a measured volume of the fluid that is stored in one or more blisters, wherein the fluid is contained within the blister, illustratively provided in a small sealed pouch within the blister, effectively forming a blister within the blister. At the appropriate time, the sealed pouch may then be ruptured, illustratively by pneumatic pressure, thereby releasing the fluid into the blister of the pouch. The instrument may also be configured the provide some or all of the reagents directly through liquid contacts between the instrument and the fitment or pouch material provided that the passage of fluid is tightly regulated by a one-way valve to prevent the instrument from becoming contaminated during a run. Further, it will often be desirable for the pouch or its fitment to be sealed after operation to prohibit contaminating DNA to escape from the pouch. Various means are known to provide reagents on demand such as syringe pumps, and to make temporary fluid contact with the fitment or pouch, such as barbed fittings or o-ring seals. It is understood that any of these methods of introducing fluids to the appropriate blister may be used with any of the embodiments of the pouch as discussed herein, as may be dictated by the needs of a particular application.

As discussed above, nested PCR involves target amplification performed in two stages. In the first-stage, targets are amplified, illustratively from genomic or reverse-transcribed template. The first-stage amplification may be terminated prior to plateau phase, if desired. In the secondary reaction, the first-stage amplicons may be diluted and a secondary amplification uses the same primers or illustratively uses nested primers hybridizing internally to the primers of the first-stage product. Advantages of nested PCR include: a) the initial reaction product forms a homogeneous and specific template assuring high fidelity in the secondary reaction, wherein even a relatively low-efficiency first-stage reaction creates adequate template to support robust second-stage reaction; b) nonspecific products from the first-stage reaction do not significantly interfere with the second stage reaction, as different nested primers are used and the original amplification template (illustratively genomic DNA or reverse-transcription product) may be diluted to a degree that eliminates its significance in the secondary amplification; and c) nested PCR enables higher-order reaction multiplexing. First-stage reactions can include primers for several unique amplification products. These products are then identified in the second-stage reactions. However, it is understood that first-stage multiplex and second-stage singleplex is illustrative only and that other configurations are possible. For example, the first-stage may amplify a variety of different related amplicons using a single pair of primers, and second-stage may be used to target differences between the amplicons, illustratively using melting curve analysis.

Figure 4:
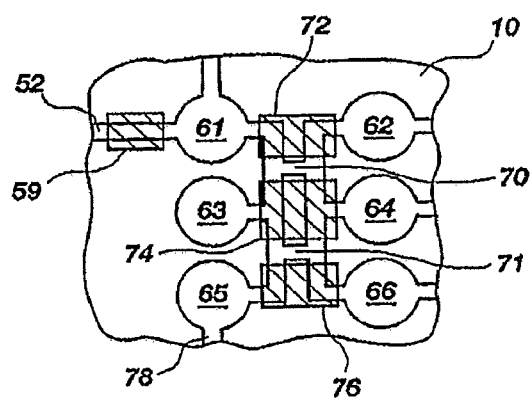
FIG. 4 shows an embodiment of the first-stage amplification zone of the flexible pouch according to FIG. 1.

Turning back to FIG. 1, the nucleic acid sample enters the first-stage amplification zone 60 via channel 52 and is delivered to blister 61. A PCR mixture, including a polymerase (illustratively a Taq polymerase), dNTPs, and primers, illustratively a plurality of pairs of primers for multiplex amplification, may be provided in blister 61 or may be introduced into blister 61 via various means, as discussed above. Alternatively, dried reagents may be spotted onto the location of blister 61 upon assembly of pouch 10, and water or buffer may be introduced to blister 61, illustratively via plunger 68, as shown in FIG. 1. As best seen in FIG. 4, the sample is now secured in blister 61 by pinch valves 59 and 72, and is thermocycled between two or more temperatures, illustratively by heat blocks or Peltier devices that are located in the instrument and configured to contact blister 61. However, it is understood that other means of heating and cooling the sample contained within blister 61, as are known in the art, are within the scope of this invention. Non-limiting examples of alternative heating/cooling devices for thermal cycling include having a air-cycled blister within the bladder, in which the air in the pneumatic blister adjacent blister 61 is cycled between two or more temperatures; or moving the sample to temperature zones within the blister 61, illustratively using a plurality of pneumatic presses, as in U.S. patent application Ser. No. 10/478,453, herein incorporated by reference, or by translating pouch 10 on an axis or providing pouch 10 with a rotary layout and spinning pouch 10 to move the contents between heat zones of fixed temperature.

Nucleic acids from pathogens are often co-isolated with considerable quantities of host nucleic acids. These host-derived nucleic acids often interact with primers, resulting in amplification of undesired products that then scavenge primers, dNTPs, and polymerase activity, potentially starving a desired product of resources. Nucleic acids from pathogenic organisms are generally of low abundance, and undesired product is a potential problem. The number of cycles in the first-stage reaction of zone 60 may be optimized to maximize specific products and minimize non-specific products. It is expected that the optimum number of cycles will be between about 10 to about 30 cycles, illustratively between about 15 to about 20 cycles, but it is understood that the number of cycles may vary depending on the particular target, host, and primer sequence.

Following the first-stage multiplex amplification, the first-stage amplification product is diluted, illustratively in incomplete PCR master mix, before fluidic transfer to secondary reaction sites.

FIG. 4 shows an illustrative embodiment for diluting the sample in three steps. In the first step, pinch valve 72 is opened and the sample undergoes a two-fold dilution by mixing the sample in blister 61 with an equal volume of water or buffer from blister 62, which is provided to blister 62, as well as blisters 64 and 66, as discussed above. Squeezing the volume back and forth between blisters 61, 62 provides thorough mixing. As above, mixing may be provided by pneumatic bladders provided in the bladder 710 and located adjacent blisters 61, 62. The pneumatic bladders may be alternately pressurized, forcing the liquid back and forth. During mixing, a pinch valve 74 prevents the flow of liquid into the adjacent blisters. At the conclusion of mixing, a volume of the diluted sample is captured in region 70, and pinch valve 72 is closed, sealing the diluted sample in region 70. Pinch valve 74 is opened and the sample is further diluted by water or buffer provided in either or both of blisters 63, 64. As above, squeezing the volume back and forth between blisters 63, 64 provides mixing. Subsequently, pinch valve 74 is closed, sealing a further diluted volume of sample in region 71. Final dilution takes place illustratively by using buffer or water provided in either or both of blisters 65, 66, with mixing as above. Illustratively this final dilution takes place using an incomplete PCR master mix (e.g., containing all PCR reagents except primers) as the fluid. Optional heating of the contents of blister 66 prior to second-stage amplification can provide the benefits of hot-start amplification without the need for expensive antibodies or enzymes. It is understood, however, that water or other buffer may be used for the final dilution, with additional PCR components provided in second-stage amplification zone 80. While the illustrative embodiment uses three dilution stages, it is understood that any number of dilution stages may be used, to provide a suitable level of dilution. It is also understood that the amount of dilution can be controlled by adjusting the volume of the sample captured in regions 70 and 71, wherein the smaller the amount of sample captured in regions 70 and 71, the greater the amount of dilution or wherein additional aliquots captured in region 70 and/or region 71 by repeatedly opening and closing pinch valves 72 and 74 and/or pinch valves 74 and 76 may be used to decrease the amount of dilution. It is expected that about $10^{-2}$ to about $10^{-5}$ dilution would be suitable for many applications.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 10 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

While dilution and second-stage sample preparation are accomplished in the illustrative embodiment by retaining a small amount of amplified sample in the blisters and channels of the first-stage PCR portion of the pouch, it is understood that these processes may also be performed in other ways. In one such illustrative example, pre-amplified sample can be captured in a small cavity in a member, illustratively a translating or rotating member, able to move a fixed volume of sample from the first to the second-stage PCR reagent. A one microliter fraction of the pre-amplified sample, mixed with 100 microliters of fresh PCR reagent would yield a one-hundred-fold reduction in concentration. It is understood that this dilution is illustrative only, and that other volumes and dilution levels are possible. This approach could be accomplished by forcing the first-stage amplification product into the rigid fitment where it contacts one of the plungers 68 or 69 of FIG. 1. In such an embodiment, the plunger would be configured to carry a small fraction of the sample into contact with the adjacent dilution buffer or second-stage PCR buffer. Similarly a sliding element could be used to carry a small amount of the first-stage amplification product into contact with the second-stage reaction mix while maintaining a seal between the stages, and containing the amplified sample within the rigid fitment 90.

Subsequent to first-stage PCR and dilution, channel 78 transfers the sample to a plurality of low volume blisters 82 for secondary nested PCR. In one illustrative embodiment, dried primers provided in the second-stage blisters are resuspended by the incoming aqueous material to complete the reaction mixture. Optionally, fluorescent dyes such as LCGreen® Plus (Idaho Technology, Salt Lake City, Utah) used for detection of double-stranded nucleic acid may be provided in each blister or may be added to the incomplete PCR master mix provided at the end of the serial dilution, although it is understood that LCGreen® Plus is illustrative only and that other dyes are available, as are known in the art. In another optional embodiment, dried fluorescently labeled oligonucleotide probes configured for each specific amplicon may be provided in each respective second-stage blister, along with the respective dried primers. Further, while pouch 10 is designed to contain all reactions and manipulations within, to reduce contamination, in some circumstances it may be desirable to remove the amplification products from each blister 82 to do further analysis. Other means for detection of the second-stage amplicon, as are known in the art, are within the scope of this invention. Once the sample is transferred to blisters 82, pinch valves 84 and 86 are activated to close off blisters 82. Each blister 82 now contains all reagents needed for amplification of a particular target. Illustratively, each blister may contain a unique pair of primers, or a plurality of blisters 82 may contain the same primers to provide a number of replicate amplifications.

It is noted that the embodiments disclosed herein use blisters for the second-stage amplification, wherein the blisters are formed of the same or similar plastic film as the rest of the flexible portion. However, in many embodiments, the contents of the second-stage blisters are never removed from the second-stage blisters, and, therefore, there is no need for the second-stage reaction to take place in flexible blisters. It is understood that the second-stage reaction may take place in a plurality of rigid, semi-rigid, or flexible chambers that are fluidly connected to the blisters. The chambers could be sealed as in the present example by placing pressure on flexible channels that connect the chambers, or may be sealed in other ways, illustratively by heat sealing or use of one-way valves. Various embodiments discussed herein include blisters provided solely for the collection of waste. Since the waste may never be removed, waste could be collected in rigid, semi-rigid, or flexible chambers.

It is within the scope of this invention to do the second-stage amplification with the same primers used in the first-stage amplification (see U.S. Pat. No. 6,605,451). However, it is often advantageous to have primers in second-stage reactions that are internal to the first-stage product such that there is no or minimal overlap between the first- and second-stage primer binding sites. Dilution of first-stage product largely eliminates contribution of the original template DNA and first-stage reagents to the second-stage reaction. Furthermore, illustratively, second-stage primers with a Tm higher than those used in the first-stage may be used to potentiate nested amplification. Primer may be designed to avoid significant hairpins, hetero/homo-dimers and undesired hybridization. Because of the nested format, second-stage primers tolerate deleterious interactions far more so than primers used to amplify targets from genomic DNA in a single step. Optionally, hot-start is used on second-stage amplification.

If a fluorescent dye is included in second-stage amplification, illustratively as a dsDNA binding dye or as part of a fluorescent probe, as are known in the art, optics provided may be used to monitor amplification of one or more of the samples. Optionally, analysis of the shape of the amplification curve may be provided to call each sample positive or negative. Illustrative methods of calling the sample are discussed in U.S. Pat. No. 6,730,501, herein incorporated by reference. Alternatively, methods employing a crossing threshold may be used. A computer may be provided externally or within the instrument and may be configured to perform the methods and call the sample positive or negative based upon the presence or absence of second-stage amplification and may provide quantitative information about the starting template concentration by comparing characteristic parameters of the amplification curve (such as crossing threshold) to standard curves, or relative to other amplification curves within the run. It is understood, however, that other methods, as are known in the art, may be used to call each sample. Other analyses may be performed on the fluorescent information. One such non-limiting example is the use of melting curve analysis to show proper melting characteristics (e.g. Tm, melt profile shape) of the amplicon. The optics provided may be configured to capture images of all blisters 82 at once, or individual optics may be provided for each individual blister. Other configurations are within the scope of this invention.

Figure 5:
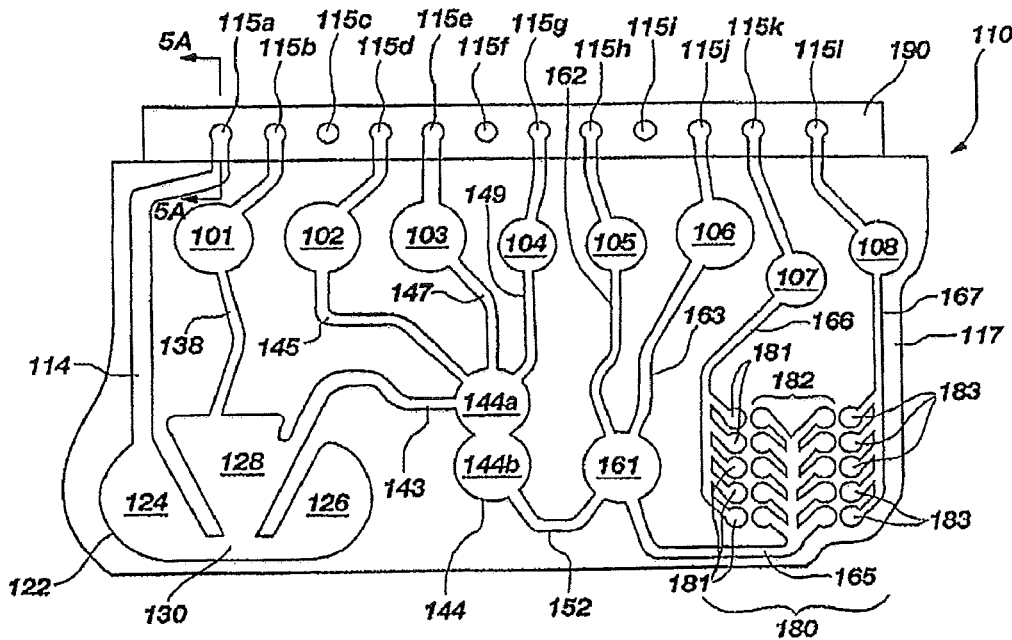
FIG. 5 is similar to FIG. 1, except showing an alternative embodiment of a pouch.
Figure 5A:
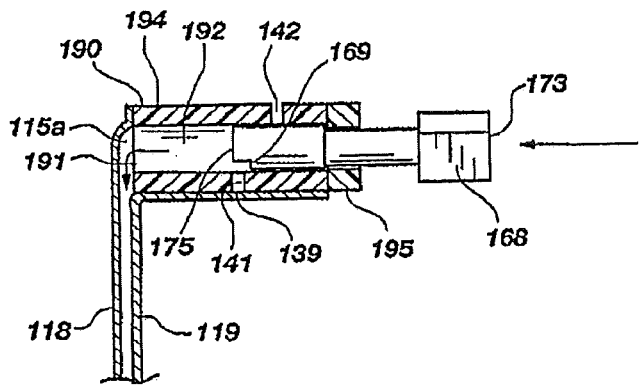
FIG. 5a is a cross-sectional view of the fitment of the pouch of FIG. 5.

FIG. 5 shows an alternative pouch 110. In this embodiment, various reagents are loaded into pouch 110 via fitment 190. FIG. 5a shows a cross-section of fitment 190 with one of a plurality of plungers 168. It is understood that, while FIG. 5a shows a cross-section through entry channel 115a, as shown in the embodiment of FIG. 5, there are 12 entry channels present (entry channel 115a through 115l), each of which may have its own plunger 168 for use in fitment 190, although in this particular configuration, entry channels 115c, 115f, and 115i are not used. It is understood that a configuration having 12 entry channels is illustrative only, and that any number of entry channels and associated plungers may be used. In the illustrative embodiment, an optional vacuum port 142 of fitment 190 is formed through a first surface 194 of fitment 190 to communicate with chamber 192. Optional vacuum port 142 may be provided for communication with a vacuum or vacuum chamber (not shown) to draw out the air from within pouch 110 to create a vacuum within chamber 192 and the various blisters and chambers of pouch 110. Plunger 168 is then inserted far enough into chamber 192 to seal off vacuum port 142. Chamber 192 is illustratively provided under a predetermined amount of vacuum to draw a desired volume of liquid into chamber 192 upon use. Additional information on preparing chamber 192 may be found in U.S. patent application Ser. No. 10/512,255, already incorporated by reference.

Illustrative fitment 190 further includes an injection port 141 formed in the second surface 195 of fitment 190. Illustratively, injection port 141 is positioned closer to the plastic film portion of pouch 110 than vacuum port 142, as shown in FIG. 5a, such that the plunger 168 is inserted far enough to seal off vacuum port 142, while still allowing access to chamber 192 via injection port 141. As shown, second surface 119 of plastic film portion 117 provides a penetrable seal 139 to prevent communication between chamber 192 and the surrounding atmosphere via injection port 141. However, it is understood that second surface 119 optionally may not extend to injection port 141 and various other seals may be employed. Further, if another location for the seal is desired, for example on a first surface 194 of fitment 190, injection port 141 may include a channel to that location on fitment 190. U.S. patent application Ser. No. 10/512,255, already incorporated by reference, shows various configurations where the seal is located remotely from the injection port, and the seal is connected to the chamber via a channel. Also, U.S. patent application Ser. No. 10/512,255 discloses various configurations where channels connect a single seal to multiple chambers. Variations in seal location, as well as connection of a single injection port to multiple chambers, are within the scope of this invention. Optionally, seal 139 may be frangible and may be broken upon insertion of a cannula (not shown), to allow a fluid sample from within the cannula to be drawn into or forced into chamber 192.

The illustrative plunger 168 of the pouch assembly 110 is cylindrical in shape and has a diameter of approximately 5 mm to be press-fit into chamber 192. Plunger 168 includes a first end portion 173 and an opposite second end portion 175. As shown in FIG. 5a, a notch 169 of plunger 168 is formed in second end portion 175. In use, second end portion 175 is inserted part way into chamber 192, and notch 169 may be aligned with injection port 141 to allow a fluid sample to be drawn into or injected into chamber 192, even when plunger 168 is inserted far enough that plunger 168 would otherwise be blocking injection port 141.

Illustratively, a fluid is placed in a container (not shown) with a syringe having a cannulated tip that can be inserted into injection port 141 to puncture seal 139 therein. In using an air-evacuated pouch assembly 110, when seal 139 is punctured, the fluid is withdrawn from the container due to the negative pressure within chamber 192 relative to ambient air pressure. Fluid then passes through port 141 to fill chamber 192. At this point, the fluid usually does not flow into the plastic film portion 117 of pouch 110. Finally, the plunger 168 is inserted into chamber 192 such that second end portion 175 of plunger 168 approaches the bottom 191 of chamber 192, to push a measured amount of the reagent or sample into the plastic film portion 117. As shown, plunger 168 is configured such that upon full insertion, second end portion 175 does not quite meet bottom 191 of chamber 192. The remaining space is useful in trapping bubbles, thereby reducing the number of bubbles entering plastic film portion 117. However, in some embodiments it may be desirable for second end portion 175 to meet bottom 191 upon full insertion of plunger 168. In the embodiment shown in FIG. 5, entry channels 115a, 115b, 115d, 115e, 115g, 115h, 115j, 115k, and 115l all lead to reaction zones or reservoir blisters. It is understood that full insertion of the plunger associated with entry channel 115a would force a sample into three-lobed blister 122, full insertion of the plunger associated with entry channel 115b would force a reagent into reservoir blister 101, full insertion of the plunger associated with entry channel 115d would force a reagent into reservoir blister 102, full insertion of the plunger associated with entry channel 115e would force a reagent into reservoir blister 103, full insertion of the plunger associated with entry channel 115g would force a reagent into reservoir blister 104, full insertion of the plunger associated with entry channel 115h would force a reagent into reservoir blister 105, full insertion of the plunger associated with entry channel 115j would force a reagent into reservoir blister 106, full insertion of the plunger associated with entry channel 115k would force a reagent into reservoir blister 107, and full insertion of the plunger associated with entry channel 115l would force a reagent into reservoir blister 108.

If a plunger design is used including notch 169 as illustrated in the embodiment shown in FIG. 5a, the plunger 168 may be rotated prior to being lowered, so as to offset notch 169 and to close off injection port 141 from communication with chamber 192, to seal the contents therein. This acts to minimize any potential backflow of fluid through injection port 141 to the surrounding atmosphere, which is particularly useful when it is desired to delay in full insertion of the plunger. Although notch 169 is shown and described above with respect to plunger 168, it is within the scope of this disclosure to close off injection port 141 soon after dispensing the fluid sample into the chamber 192 by other means, such as depressing plunger 168 toward the bottom of chamber 192, heat sealing, unidirectional valves, or self-sealing ports, for example. If heat sealing is used as the sealing method, a seal bar could be included in the instrument such that all chambers are heat sealed upon insertion of the pouch into the instrument.

Figure 6:
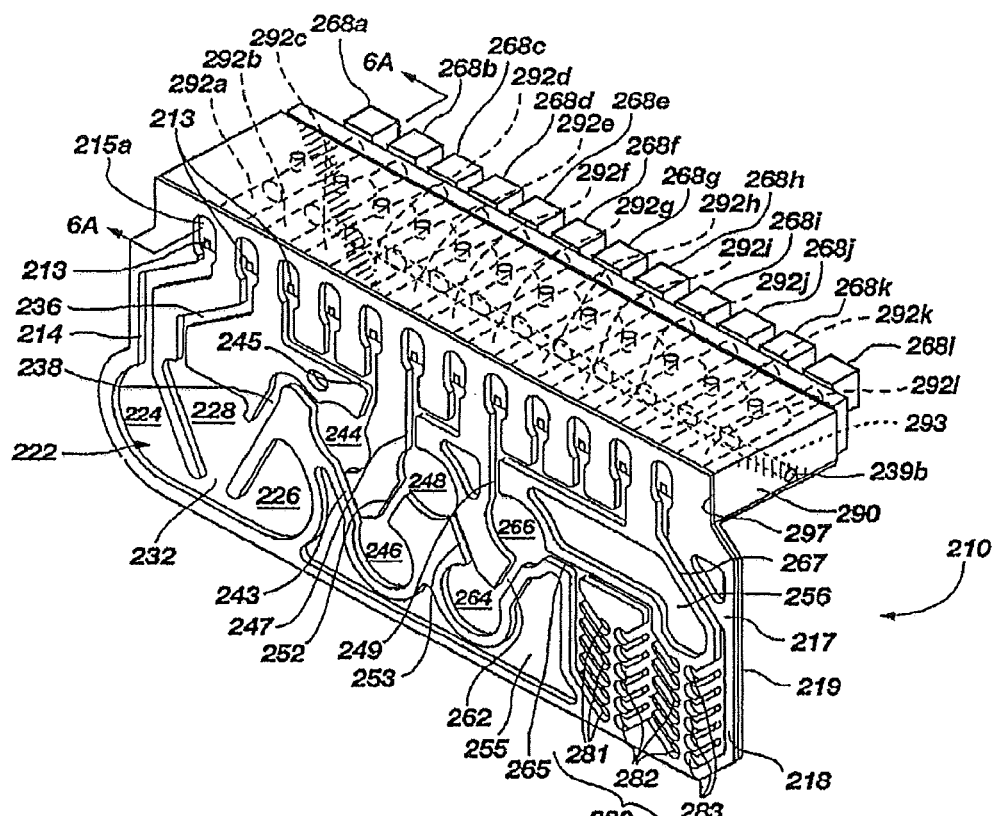
FIG. 6 is a perspective view of another alternative embodiment of a pouch.
Figure 6A:
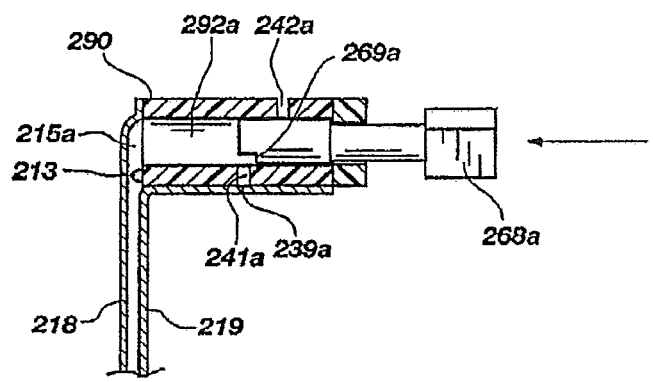
FIG. 6a is a cross-sectional view of the fitment of the pouch of FIG. 6.

In the illustrative method, the user injects the sample into the injection port 141 associated with entry channel 115a, and water into the various other injection ports. The water rehydrates reagents that have been previously freeze-dried into chambers 192 associated with each of entry channels 115b, 115d, 115e, 115g, 115h, 115j, 115k, and 115l. The water may be injected through one single seal and then be distributed via a channel to each of the chambers, as shown in FIG. 6 below, or the water could be injected into each chamber independently. Alternatively, rather than injecting water to rehydrate dried reagents, wet reagents such as lysis reagents, nucleic acid extraction reagents, and PCR reagents may be injected into the appropriate chambers 192 of the fitment 190.

Figure 8:
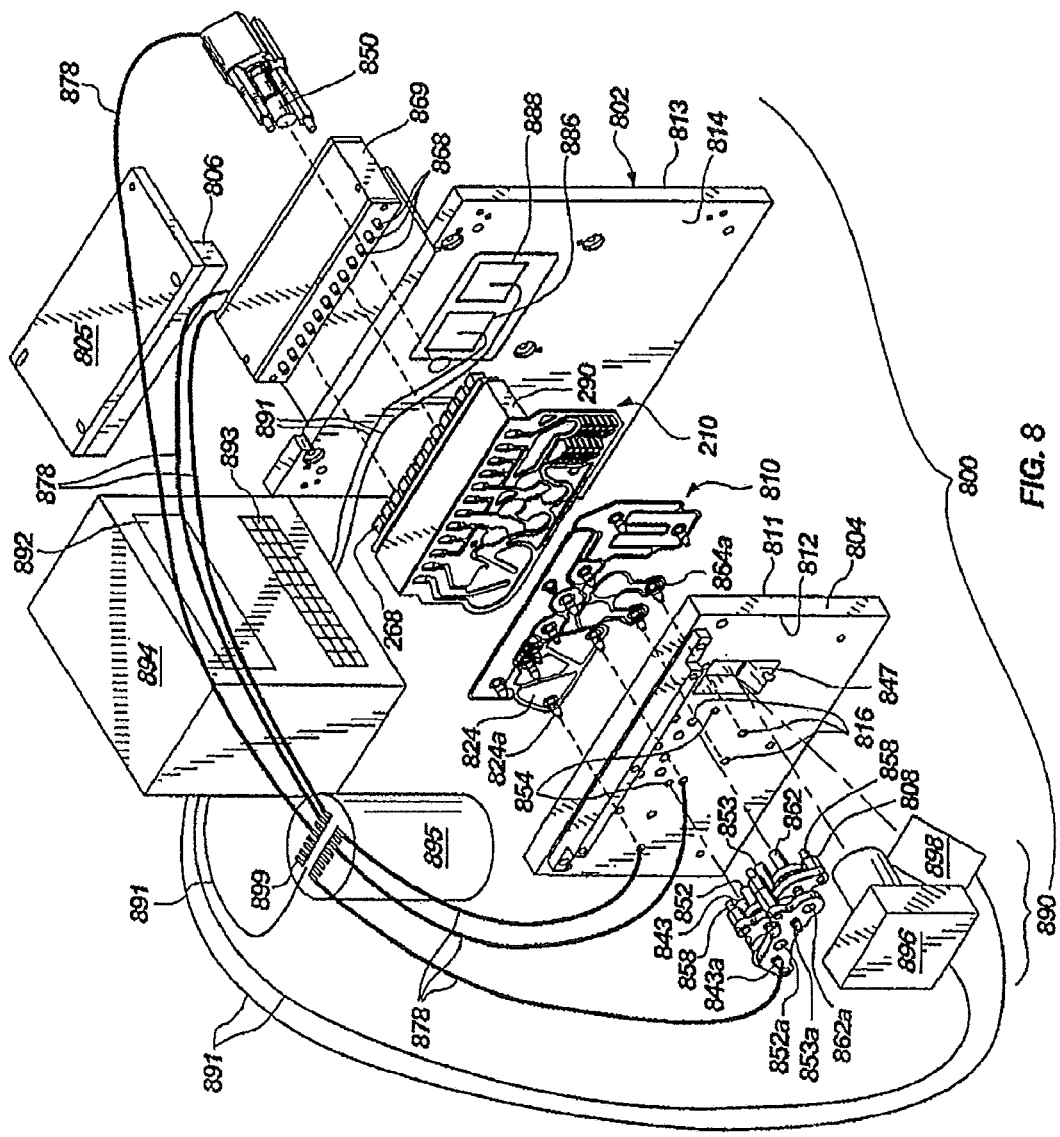
FIG. 8 is an exploded perspective view of an instrument for use with the pouch of FIG. 6, including the pouch of FIG. 6.

Upon activation of the plunger 168 associated with entry channel 115a, the sample is forced directly into three-lobed blister 122 via channel 114. The user also presses the remaining plungers 168, forcing the contents out of each of the chambers 192 in fitment 190 and into reservoir blisters 101 through 108. At this point, pouch 110 is loaded into an instrument for processing. While instrument 800, shown in FIG. 8, is configured for the pouch 210 of FIG. 6, it is understood that modification of the configuration of the bladders of instrument 800 would render instrument 800 suitable for use with pouches 110 and 510, or with pouches of other configurations.

In one illustrative example, upon depression of the plungers 168, reservoir blister 101 now contains DNA-binding magnetic beads in isopropanol, reservoir blister 102 now contains a first wash solution, reservoir blister 103 now contains a second wash solution, reservoir blister 104 now contains a nucleic acid elution buffer, reservoir blister 105 now contains first-stage PCR reagents, including multiplexed first-stage primers, reservoir blister 106 now contains second-stage PCR reagents without primers, reservoir blister 107 now contains negative control PCR reagents without primers and without template, and reservoir blister 108 now contains positive control PCR reagents with template. However, it is understood that these reagents are illustrative only, and that other reagents may be used, depending upon the desired reactions and optimization conditions.

Once pouch 110 has been placed into instrument 800 and the sample has been moved to three-lobed blister 122, the sample may be subjected to disruption by agitating the sample with lysing particles such as ZS or ceramic beads. The lysing particles may be provided in three-lobed blister 122, or may be injected into three-lobed blister 122 along with the sample. The three-lobed blister 122 of FIG. 5 is operated in much the same way as three-lobed blister 22 of FIG. 1, with the two lower lobes 124, 126 pressurized together, and pressure is alternated between the upper lobe 128 and the two lower lobes 124, 126. However, as illustrated, lower lobes 124, 126 are much more rounded than lower lobes 24, 26, allowing for a smooth flow of beads to channel 130 and allowing for high-speed collisions, even without the triangular flow separator at nexus 32. As with three-lobed blister 22, three-lobed blister 122 of FIG. 5 allows for effective lysis or disruption of microorganisms, cells, and viral particles in the sample. It has been found that a channel 130 having a width of about 3-4 mm, and illustratively about 3.5 mm, remains relatively clear of beads during lysis and is effective in providing for high-velocity collisions.

After lysis, nucleic-acid-binding magnetic beads are injected into upper lobe 128 via channel 138 by pressurizing a bladder positioned over reservoir blister 101. The magnetic beads are mixed, illustratively more gently than with during lysis, with the contents of three-lobed blister 122, and the solution is incubated, illustratively for about 1 minute, to allow nucleic acids to bind to the beads.

The solution is then pumped into the "FIG. 8" blister 144 via channel 143, where the beads are captured by a retractable magnet housed in the instrument, which is illustratively pneumatically driven. The bead capture process begins by pressurizing all lobes 124, 126, and 128 of the bead milling apparatus 122. This forces much of the liquid contents of 122 through channel 143 and into blister 144. A magnet is brought into contact with the lower portion 144b of blister 144 and the sample is incubated for several seconds to allow the magnet to capture the beads from the solution, then the bladders adjacent to blister 122 are depressurized, the bladders adjacent blister portions 144a and 144b are pressurized, and the liquid is forced back into blister 122. Since not all of the beads are captured in a single pass, this process may be repeated up to 10 times to capture substantially all of the beads in blister 144. Then the liquid is forced out of blister 144, leaving behind only the magnetic beads and the captured nucleic acids, and wash reagents are introduced into blister 144 in two successive washes (from reservoir blisters 102 and 103 via channels 145 and 147, respectively). In each wash, the bladder positioned over the reservoir blister containing the wash reagent is pressurized, forcing the contents into blister 144. The magnet is withdrawn and the pellet containing the magnetic beads is disrupted by alternatively pressurizing each of two bladders covering each lobe 144a and 144b of blister 144. When the upper lobe 144a is compressed, the liquid contents are forced into the lower lobe 144b, and when the lower lobe 144b is compressed, the contents are forced into the upper lobe 144a. By agitating the solution in blister 144 between upper lobe 144a and lower lobe 144b, the magnetic beads are effectively washed of impurities. A balance is maintained between inadequate agitation, leaving the pellet of beads undisturbed, and excessive agitation, potentially washing the nucleic acids from the surface of the beads and losing them with the wash reagents. After each wash cycle, the magnetic beads are captured via the magnet in blister 144 and the wash reagents are illustratively forced into three-lobed blister 122, which now serves as a waste receptacle. However, it is understood that the used reservoir blisters may also serve as waste receptacles, or other blisters may be provided specifically as waste receptacles.

Nucleic acid elution buffer from reservoir blister 104 is then injected via channel 149 into blister 144, the sample is once again agitated, and the magnetic beads are recaptured by employment of the magnet. The fluid mixture in blister 144 now contains nucleic acids from the original sample. Pressure on blister 144 moves the nucleic acid sample to the first stage PCR blister 161 via channel 152, where the sample is mixed with first-stage PCR master mix containing multiple primer sets, the PCR master mix provided from reservoir blister 105 via channel 162. If desired, the sample and/or the first-stage PCR master mix may be heated prior to mixing, to provide advantages of hot start. Optionally, components for reverse transcription of RNA targets may be provided prior to first-stage PCR. Alternatively, an RT enzyme, illustratively a thermostable RT enzyme may be provided in the first-stage PCR master mix to allow for contemporaneous reverse transcription of RNA targets. It is understood that an RT enzyme may be present in the first-stage PCR mixture in any of the embodiments disclosed herein. As will be seen below, pouch 110 of FIG. 5 is configured for up to 10 primer sets, but it is understood that the configuration may be altered and any number of primer sets may be used. A bladder positioned over blister 161 is pressurized at low pressure, to force the contents of blister 161 into intimate contact with a heating/cooling element, illustratively a Peltier element, on the other side of blister 161. The pressure on blister 161 should be sufficient to assure good contact with the heating/cooling element, but should be gentle enough such that fluid is not forced from blister 161. The heating/cooling element is temperature cycled, illustratively between about 60° C. to about 95° C. Illustratively, temperature cycling is performed for about 15-20 cycles, resulting in amplification of one or more nucleic acid targets present. Also illustratively, temperature cycling ceases prior to plateau phase, and may cease in log phase or even prior to log phase. In one example, it may be desirable merely to enrich the sample with the desired amplicons, without reaching minimal levels of detection. See U.S. Pat. No. 6,605,451, herein incorporated by reference.

The amplified sample is optionally then diluted by forcing most the sample back into blister 144 via channel 152, leaving only a small amount (illustratively about 1 to 5%) of the amplified sample in blister 161, and second-stage PCR master mix is provided from reservoir blister 106 via channel 163. The sample is thoroughly mixed illustratively by moving it back and forth between blisters 106 and 161 via channel 163. If desired, the reaction mixture may be heated to above extension temperature, illustratively at least 60° C., prior to second-stage amplification. The sample is then forced through channel 165 into an array of low volume blisters 182 in the center of second-stage amplification zone 180. Each of the ten illustrative low volume blisters 182 may contain a different primer pair, either essentially the same as one of the primer pairs in the first-stage amplification, or "nested" within the first-stage primer pair to amplify a shortened amplicon. The primers, now hydrated by the sample, complete the amplification mixture. Positive and negative control samples are also introduced by pressurizing the contents of reservoir blisters 107 and 108, respectively, forcing PCR master mix either without target DNA from reservoir blister 107 via channel 166, or with control DNA from reservoir blister 108, via channel 167. As illustrated, there are five each of positive control blisters 183 and negative control blisters 181, which may be multiplexed 2-fold to provide the necessary controls for ten different second-stage amplification reactions. It is understood that this configuration is illustrative only and that any number of second-stage blisters may be provided.

Figure 5B:
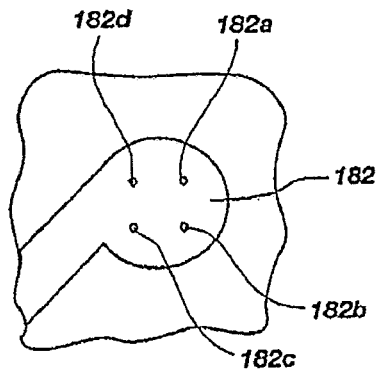
FIG. 5b is an enlargement of a portion of the pouch of FIG. 5.

Illustratively, the PCR master mix used for second-stage amplification lacks the primers, but is otherwise complete. However, an "incomplete" PCR master mix may lack other PCR components as well. In one example, the second-stage PCR master mix is water or buffer only, which is then mixed with the optionally diluted first-stage PCR amplification product. This mixture is moved to the small-volume PCR reaction blisters, where all of the remaining components have been previously provided. If desired, all of the remaining components may be mixed together and spotted as a single mixture into the small-volume PCR reaction blisters. Alternatively, as illustrated in FIG. 5b, each of the components may be spotted onto a separate region of the small-volume PCR reaction blister 182. As shown in FIG. 5*b*, four regions are present, illustratively with dNTPs spotted at region 182*a*, primers spotted at 182*b*, polymerase spotted at 182*c*, and a magnesium compound spotted at 182*d*. By spotting the components separately and heating the sample mixture prior to rehydrating the components, nonspecific reactions can be minimized. It is understood that any combination of components can be spotted this way, and that this method of spotting components into one or more regions of the blisters may be used with any embodiment of the present invention.

The channels 165, 166, and 167 leading to the small-volume PCR reaction blisters 181, 182, and 183 are sealed, and a pneumatic bladder gently presses the array against a heating/cooling element, illustratively a Peltier element, for thermal cycling. The cycling parameters may be independently set for second-stage thermal cycling. Illustratively, the reactions are monitored by focusing an excitation source, illustratively a blue light (450-490 nm), onto the array, and imaging the resultant fluorescent emissions, illustratively fluorescent emissions above 510 nm.

In the above example, pinch valves are not discussed. However, it is understood that when it is desired to contain a sample in one of the blisters, pneumatic actuators positioned over channels leading to and from the particular blister are pressurized, creating pinch valves and closing off the channels. Conversely, when it is desired to move a sample from one of the blisters, the appropriate pneumatic actuator is depressurized, allowing the sample flow through the channel.

The pouch described above in FIG. 5 includes reagent reservoir blisters 101 through 108, in which the user injected reagents from the fitment 190 into the reagent reservoir blisters 101 through 108 in the plastic film portion 117 of the pouch 110, illustratively prior to insertion of pouch 110 into the instrument. While there are advantages to the use of the reagent reservoir blisters of FIG. 5, including having the ability to maintain the contents of the various blisters at different temperatures, there are some disadvantages as well. Because the operator is responsible for moving the reagents from the fitment 190 to the reservoir blisters 101 through 108, and because this is often done outside of the machine and thus without activated pinch valves, reagents could occasionally leak from the reservoir blisters to the working blisters. The reagents in reservoir blisters are exposed during preparation and loading. If they are pressed, squeezed, or even lightly bumped, the reagents may leak through available channels. If the loss of reagents is substantial, the reaction may fail completely. Furthermore, during operation there may be some variability in the amount of reagent forced from the reservoir blisters 101 through 108, leading to inconsistent results. Automation of introduction of the reagents to fitment 190 and movement of the reagents from fitment 190 to reagent reservoir blisters 101 through 108 would solve many of these problems, and is within the scope of this invention.

The pouch 210 of FIG. 6 addresses many of these issues in a different way, by using a direct-injection approach wherein the instrument itself moves the plungers 268, illustratively via pneumatic pistons, and forces the reagents into the various working blisters as the reagents are needed. Rather than storing the reagents in reservoir blisters 101 through 108 of FIG. 5, in the embodiment of FIG. 6 the reagents are introduced into various chambers 292 of fitment 290 and are maintained there until needed. Pneumatic operation of piston 268 at the appropriate time introduces a measured amount of the reagent to the appropriate reaction blister. In addition to addressing many of the above-mentioned issues, pouch 210 also has a much more compact shape, allowing for a smaller instrument design, and pouch 210 has shorter channels, permitting better fluid flow and minimizing reagent loss in channels.

In one illustrative embodiment of FIG. 6, a 300 µl mixture comprising the sample to be tested (100 µl) and lysis buffer (200 µl) is injected into injection port 241*a*. Water is also injected into the fitment 290 via seal 239*b*, hydrating up to eleven different reagents, each of which were previously provided in dry form in chambers 292*b* through 292*l* via channel 293 (shown in shadow). These reagents illustratively may include freeze-dried PCR reagents, DNA extraction reagents, wash solutions, immunoassay reagents, or other chemical entities. For the example of FIG. 6, the reagents are for nucleic acid extraction, first-stage multiplex PCR, dilution of the multiplex reaction, and preparation of second-stage PCR reagents, and control reactions. In the embodiment shown in FIG. 6, all that need be injected is the sample in port 241*a* and water in port 241*b*.

As shown in FIG. 6, water injected via seal 293*b* is distributed to various chambers via channel 293. In this embodiment, only the sample and water need be injected into pouch 210. It is understood, however, that water could be injected into each chamber 292 independently. Further, it is understood that, rather than providing dried reagents in the various chambers 292 and hydrating upon injection of the water, specific wet reagents could be injected into each chamber, as desired. Additionally, it is understood that one or more of chambers 292 could be provided with water only, and the necessary reagents may be provided dried in the appropriate reaction blisters. Various combinations of the above, as dictated by the needs of the particular reaction, are within the scope of this invention.

As seen in FIG. 6, optional protrusions 213 are provided on bottom surface 297 of fitment 290. As shown, protrusions 213 are located within their respective entry channels 215. However, other configurations are possible. Protrusions 213 assist in opening entry channel 215 and prevent bottom surface 297 from engaging another flat surface in such a way to pinch off entry channels 215 when plungers 268 are depressed, which helps prevent back-flow upon activation of the plungers 268. Such protrusions may be used on any of the various pouches according to the present invention.

In embodiments wherein water is injected into the pouch to hydrate multiple dry reagents in multiple chambers in the fitment, a means of closing the channel between the injection port and the many chambers is desired. If the channel is not closed, activation of each plunger may force some of the contents of its respective chamber back out into the channel, potentially contaminating neighboring chambers and altering the volumes contained in and delivered from the chamber. Several ways of closing this channel have been used, including rotating a notched plunger 268 as discussed above, and heat-sealing the plastic film across the channel thereby closing the channel permanently, and applying pressure to the channel as a pinch valve. Other closures may also be used, such as valves built into the fitment, illustratively one-way valves.

Figure 7:
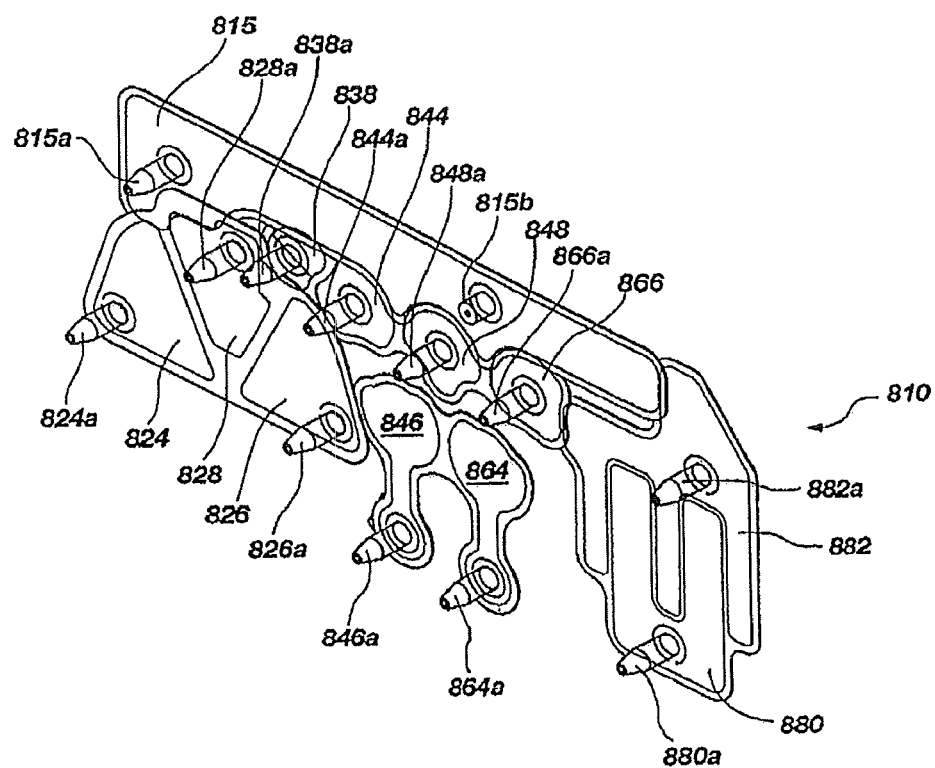
FIG. 7 shows illustrative bladder components for use with the pouch of FIG. 6.

After the fluids are loaded into chambers 292 and pouch 210 is loaded into the instrument, plunger 268*a* is depressed illustratively via activation of a pneumatic piston, forcing the balance of the sample into three-lobed blister 220 via channel 214. As with the embodiments shown in FIGS. 1 and 5, the lobes 224, 226, and 228 of three-lobed blister 220 are sequentially compressed via action bladders 824, 826, and 828 of bladder assembly 810, shown in FIGS. 7-9, forcing the liquid through the narrow nexus 232 between the lobes, and driving high velocity collisions, shearing the sample and liberating nucleic acids, illustratively including nucleic acids from hard-to-open spores, bacteria, and fungi. Cell lysis continues for an appropriate length of time, illustratively 0.5 to 10 minutes.

Once the cells have been adequately lysed, plunger 268b is activated and nucleic acid binding magnetic beads stored in chamber 292b are injected via channel 236 into upper lobe 228 of three-lobed blister 220. The sample is mixed with the magnetic beads and the mixture is allowed to incubate for an appropriate length of time, illustratively approximately 10 seconds to 10 minutes.

The mixture of sample and beads are forced through channel 238 into blister 244 via action of bladder 826, then through channel 243 and into blister 246 via action of bladder 844, where a retractable magnet 850 located in instrument 800 adjacent blister 245, shown in FIG. 8, captures the magnetic beads from the solution, forming a pellet against the interior surface of blister 246. A pneumatic bladder 846, positioned over blister 246 then forces the liquid out of blister 246 and back through blister 244 and into blister 222, which is now used as a waste receptacle. However, as discussed above with respect to FIG. 5, other waste receptacles are within the scope of this invention. One of plungers 268c, 268d, and 268e may be activated to provide a wash solution to blister 244 via channel 245, and then to blister 246 via channel 243. Optionally, the magnet 850 is retracted and the magnetic beads are washed by moving the beads back and forth from blisters 244 and 246 via channel 243, by alternatively pressurizing bladders 844 and 846. Once the magnetic beads are washed, the magnetic beads are recaptured in blister 246 by activation of magnet 850, and the wash solution is then moved to blister 222. This process may be repeated as necessary to wash the lysis buffer and sample debris from the nucleic acid-binding magnetic beads. Illustratively, three washes are done, one each using wash reagents in chambers 292c, 292d, and 292e. However, it is understood that more or fewer washes are within the scope of this invention. If more washes are desired, more chambers 292 may be provided. Alternatively, each chamber 292 may hold a larger volume of fluid and activation of the plungers may force only a fraction of the volume from the chamber upon each activation.

After washing, elution buffer stored in chamber 292f is moved via channel 247 to blister 248, and the magnet is retracted. The solution is cycled between blisters 246 and 248 via channel 252, breaking up the pellet of magnetic beads in blister 246 and allowing the captured nucleic acids to dissociate from the beads and come into solution. The magnet 850 is once again activated, capturing the magnetic beads in blister 246, and the eluted nucleic acid solution is forced into blister 248.

Plunger 268h is depressed and first-stage PCR master mix from chamber 292h is mixed with the nucleic acid sample in blister 248. Optionally, the mixture is mixed by alternative activation of bladders 848 and 864, forcing the mixture between 248 and 264 via channel 253. After several cycles of mixing, the solution is contained in blister 264, where first-stage multiplex PCR is performed. If desired, prior to mixing, the sample may be retained in blister 246 while the first-stage PCR master mix is pre-heated, illustratively by moving the first-stage PCR master mix into blister 264 or by providing a heater adjacent blister 248. As discussed above, this pre-heating may provide the benefits of hot start PCR. The instrument 800 illustrated in FIG. 8 features Peltier-based thermal cyclers 886 and 888 which heat and cool the sample. However, it is understood that other heater/cooler devices may be used, as discussed above. Optionally, mixing between blisters 248 and 264 may continue during temperature cycling, with thermal cycler 886 positioned to heat and cool both blisters 248 and 264. It has been found that such mixing improves the first-stage PCR reaction in some embodiments. Also, thermal cycling can be accomplished by varying the temperatures in two or more different blisters, allowing minimal energy expenditure and maximizing thermal cycling speed. For example the temperature can be maintained at 95° C. in blister 248, and 65° C. blister 264, and moving the sample between these blisters effectively transfers heat into and out of the sample, allowing rapid and accurate thermal cycling. Temperature cycling is illustratively performed for 15-20 cycles, although other levels of amplification may be desirable, depending on the application, as discussed above. As will be seen below, the second-stage amplification zone 280 is configured to detect amplification in 18 second-stage reactions. Accordingly, 18 different primer-pairs may be included in the PCR reaction in blister 264.

In an alternative hot start method, pouch 210 is manufactured with the primers provided in one of the blisters, illustratively blister 264. In one embodiment, the primers are freeze dried separately and then introduced during manufacture into blister 264 as a friable pellet. Prior to first-stage PCR, illustratively the sample is eluted from blister 246 and pushed to blister 264 to rehydrate the primer pellet. Peltier 886, which is positioned adjacent blisters 248 and 264 is heated to 48° C., and PCR master mix is pushed to blister 248. After a hold, illustratively for 10 seconds, during which the two blisters reach 48° C., mixing between blisters 248 and 264 begins. Thus, the enzymes and dNTPs remain in blister 248 and most of the sample and the primers remain in blister 264 until the components separately have reached 48° C. It is understood, however, that the choice of 48° C. was made for use with concurrent first-stage amplification and RT using AMV, which is active up to 50° C. If RT is not needed or a more thermostable RT enzyme is used, then one or both of the two blisters 248 and 264 may be heated up to 58° C., or even higher, depending on the primer melting temperature or other factors in a particular first-stage amplification protocol. It is understood that this hot start method may be used with any embodiment of the present invention.

In an alternative embodiment, to reduce the complexity of the first-stage PCR reaction, blister 248 may be divided into two or more blisters. It is believed that the number of nonspecific products of a multiplex reaction goes up as the square (or possibly higher power) of the number of primers in the mixture, while the loss of sensitivity of an assay is a linear function of the amount of input sample. Thus, for example, splitting the first stage PCR into two reactions, each of half the volume of the single reaction of this embodiment, would reduce sensitivity by two-fold but the quantity and complexity of the nonspecific reactions would be ¼ as much. If blister 248 is divided into or more blisters, blister 264 may be divided into a number of blisters equal to the number of blisters 248. Each respective blister 248 would be connected to its respective blister 264 via a respective channel 253. Each blister 264 would be provided with a pellet comprising a subset of all primers. Sample from blister 246 would be divided across each blister 248, each blister 248 would be sealed from all others, and thermal cycling would proceed with each pair of blisters 248 and 264, as described above. After thermal cycling, the sample would be recombined into blister 266 or individually sent to separate sets of second-stage blisters.

After first-stage PCR has proceeded for the desired number of cycles, the sample may be diluted as discussed above with respect to the embodiment of FIG. 5, by forcing most of the sample back into blister 248, leaving only a small amount, and adding second-stage PCR master mix from chamber 292*i*. Alternatively, a dilution buffer from 292*i* may be moved to blister 266 via channel 249 and then mixed with the amplified sample in blister 264 by moving the fluids back and forth between blisters 264 and 266. After mixing, a portion of the diluted sample remaining in blister 264 is forced away to three-lobed blister 222, now the waste receptacle. If desired, dilution may be repeated several times, using dilution buffer from chambers 292*j* and 292*k*, and then adding second-stage PCR master mix from chamber 292*g* to some or all of the diluted amplified sample. It is understood that the level of dilution may be adjusted by altering the number of dilution steps or by altering the percentage of the sample discarded prior to mixing with the dilution buffer or second-stage PCR master mix. If desired, this mixture of the sample and second-stage PCR master mix may be pre-heated in blister 264 prior to movement to second-stage blisters 282 for second-stage amplification. As discussed above, such preheating may obviate the need for a hot-start component (antibody, chemical, or otherwise) in the second-stage PCR mixture.

The illustrative second-stage PCR master mix is incomplete, lacking primer pairs, and each of the 18 second-stage blisters 282 is pre-loaded with a specific PCR primer pair. If desired, second-stage PCR master mix may lack other reaction components, and these components may then be pre-loaded in the second-stage blisters 282 as well. As discussed above with the prior examples, each primer pair may be identical to a first-stage PCR primer pair or may be nested within the first-stage primer pair. Movement of the sample from blister 264 to the second-stage blisters completes the PCR reaction mixture. Control samples from chamber 292*l* are also moved to control blisters 283 via channel 267. The control samples may be positive or negative controls, as desired. Illustratively, each pouch would contain control reactions that validate the operation of each step in the process and demonstrate that positive results are not the result of self-contamination with previously amplified nucleic acids. However, this is not practical in many protocols, particularly for a highly multiplexed reaction. One illustrative way of providing suitable controls involves spiking samples with a species such as baker's yeast. The nucleic acids are extracted from the yeast, alongside other nucleic acids. First- and second-stage PCR reactions amplify DNA and/or RNA targets from the yeast genome. Illustratively, an mRNA sequence derived from a spliced pre-mRNA can be used to generate an RNA-specific target sequence by arranging the primer sequences to span an intron. A quantative analysis of the yeast copy number against reference standards allows substantial validation that each component of the system is working. Negative control reactions for each of the many second-stage assays are more problematic. It may be desirable to run control reactions either in parallel or in a separate run.

Activation of bladder 882 of bladder assembly 810 seals the samples into their respective second-stage blisters 282, 283, and activation of bladder 880 provides gentle pressure on second-stage blisters 282, 283, to force second-stage blisters 282, 283 into contact with a heater/cooler device. A window 847 positioned over the second-stage amplification zone 280 allows fluorescence monitoring of the array during PCR and during a DNA melting-curve analysis of the reaction products.

It is noted that the pouch 210 of FIG. 6 has several unsealed areas, such as unsealed area 255 and unsealed area 256. These unsealed areas form blisters that are not involved in any of the reactions in this illustrative embodiment. Rather, these unsealed areas are provided in space between the working blisters and channels. In some manufacturing processes, as compared to pouches that are sealed in all unused space, it has been found that fewer leaks sometimes result when unsealed areas such as 255 and 256 are provided, presumably by reducing problematic wrinkles in the film material. Such unsealed areas optionally may be provided on any pouch embodiment.

FIG. 8 shows an illustrative apparatus 800 that could be used with pouch 210. Instrument 800 includes a support member 802 that could form a wall of a casing or be mounted within a casing. Instrument 800 also includes a second support member 804 that is optionally movable with respect to support member 802, to allow insertion and withdrawal of pouch 210. Movable support member 804 may be mounted on a track or may be moved relative to support member 802 in any of a variety of ways. Illustratively, a lid 805 fits over pouch 210 once pouch 210 has been inserted into instrument 800. In another embodiment, both support members 802 and 804 may be fixed, with pouch 210 held into place by other mechanical means or by pneumatic pressure.

Illustratively, the bladder assembly 810 and pneumatic valve assembly 808 are mounted on movable member 802, while the heaters 886 and 888 are mounted on support member 802. However, it is understood that this arrangement is illustrative only and that other arrangements are possible. As bladder assembly 810 and pneumatic valve assembly 808 are mounted on movable support member 804, these pneumatic actuators may be moved toward pouch 210, such that the pneumatic actuators are placed in contact with pouch 210. When pouch 210 is inserted into instrument 800 and movable support member 804 is moved toward support member 802, the various blisters of pouch 210 are in a position adjacent to the various pneumatic bladders of bladder assembly 810 and the various pneumatic pistons of pneumatic valve assembly 808, such that activation of the pneumatic actuators may force liquid from one or more of the blisters of pouch 210 or may form pinch valves with one or more channels of pouch 210. The relationship between the blisters and channels of pouch 210 and the pneumatic actuators of bladder assembly 810 and pneumatic valve assembly 808 are discussed in more detail below with respect to FIGS. 9 and 10.

Each pneumatic actuator has one or more pneumatic fittings. For example, bladder 824 of bladder assembly 810 has pneumatic fitting 824*a* and pneumatic piston 843 has its associated pneumatic fitting 843*a*. In the illustrative embodiment, each of the pneumatic fittings of bladder assembly 810 extends through a passageway 816 in movable support member 804, where a hose 878 connects each pneumatic fitting to compressed air source 895 via valves 899. In the illustrative embodiment, the passageways 816 not only provide access to compressed air source 895, but the passageways also aid in aligning the various components of bladder assembly 810, so that the bladders align properly with the blisters of pouch 210.

Similarly, pneumatic valve assembly 808 is also mounted on movable support member 804, although it is understood that other configurations are possible. In the illustrative embodiment, pins 858 on pneumatic valve assembly 808 mount in mounting openings 859 on movable support member 804, and pneumatic pistons 843, 852, 853, and 862 extend through passageways 816 in movable support member 804, to contact pouch 210. As illustrated, bladder assembly is mounted on a first side 811 of movable support member 804 while pneumatic valve assembly 808 is mounted on a second side 812 of movable support member 804. However, because pneumatic pistons 843, 852, 853, and 862 extend through passageways 816, the pneumatic pistons of pneumatic valve assembly 808 and the pneumatic bladders of bladder assembly 810 work together to provide the necessary pneumatic actuators for pouch 210.

As discussed above, each of the pneumatic actuators of bladder assembly 810 and pneumatic valve assembly 808 has an associated pneumatic fitting. While only several hoses 878 are shown in FIG. 8, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Several other components of instrument 810 are also connected to compressed gas source 895. Magnet 850, which is mounted on a first side 813 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 246 of pouch 210. However, depending on the material of support member 802, it is understood that recess 851 need not extend all the way through support member 802, as long as when magnet 850 is deployed, magnet 850 is close enough to provide a sufficient magnetic field at blister 246, and when magnet 850 is retracted, magnet 850 does not significantly affect any magnetic beads present in blister 246. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869, which is mounted on support 802, are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown. When the pouch 210 is inserted into instrument 800, the twelve pneumatic pistons 868 are positioned to activate their respective twelve plungers 268 of pouch 210. When lid 805 is closed over pouch 210, a lip 806 on lid 805 provides a support for fitment 290, so that as the pneumatic pistons 868 are activated, lid 805 holds fitment 290 in place. It is understood that other supports for fitment 290 are within the scope of this invention.

A pair of heating/cooling devices, illustratively Peltier heaters, are mounted on a second side 814 of support 802. First-stage heater 886 is positioned to heat and cool the contents of blister 264 for first-stage PCR. Second-stage heater 888 is positioned to heat and cool the contents of second-stage blisters 282 and 283 of pouch 210, for second-stage PCR. It is understood, however, that these heaters could also be used for other heating purposes, and that other heaters may be included, as appropriate for the particular application.

If desired, a feedback mechanism (not shown) may be included in instrument 800 for providing feedback regarding whether the sample has actually been forced into a particular blister. Illustrative feedback mechanisms include temperature or pressure sensors or optical detectors, particularly if a fluorescent or colored dye is included. Such feedback mechanisms illustratively may be mounted on either of support members 802 or 804. For example, a pressure sensor may be mounted on support 802 adjacent the location of blister 264. When the sample is supposedly moved to blister 264, if the pressure sensor is depressed, then sample processing is allowed to continue. However, if the pressure sensor is not depressed, then sample processing may be stopped, or an error message may be displayed on screen 892. Any combination or all of the blisters may have feedback mechanisms to provide feedback regarding proper movement of the sample through the pouch.

When fluorescent detection is desired, an optical array 890 may be provided. As shown in FIG. 8, optical array 890 includes a light source 898, illustratively a filtered LED light source, filtered white light, or laser illumination, and a camera 896. A window 847 through movable support 804 provides optical array 890 with access to second-stage amplification zone 280 of pouch 210. Camera 896 illustratively has a plurality of photodetectors each corresponding to a second-stage blister 282, 823 in pouch 210. Alternatively, camera 896 may take images that contain all of the second-stage blisters 282, 283, and the image may be divided into separate fields corresponding to each of the second-stage blisters 282, 283. Depending on the configuration, optical array 890 may be stationary, or optical array 890 may be placed on movers attached to one or more motors and moved to obtain signals from each individual second-stage blister 282, 283. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 890 or may be external to instrument 890. Further, computer 894 may include built-in circuit boards that control some or all of the components, and may also include an external computer, such as a desktop or laptop PC, to receive and display data from the optical array. An interface 893, illustratively a keyboard interface, may be provided including keys for inputting information and variables such as temperatures, cycle times, etc. Illustratively, a display 892 is also provided. Display 892 may be an LED, LCD, or other such display, for example.

Figure 9:
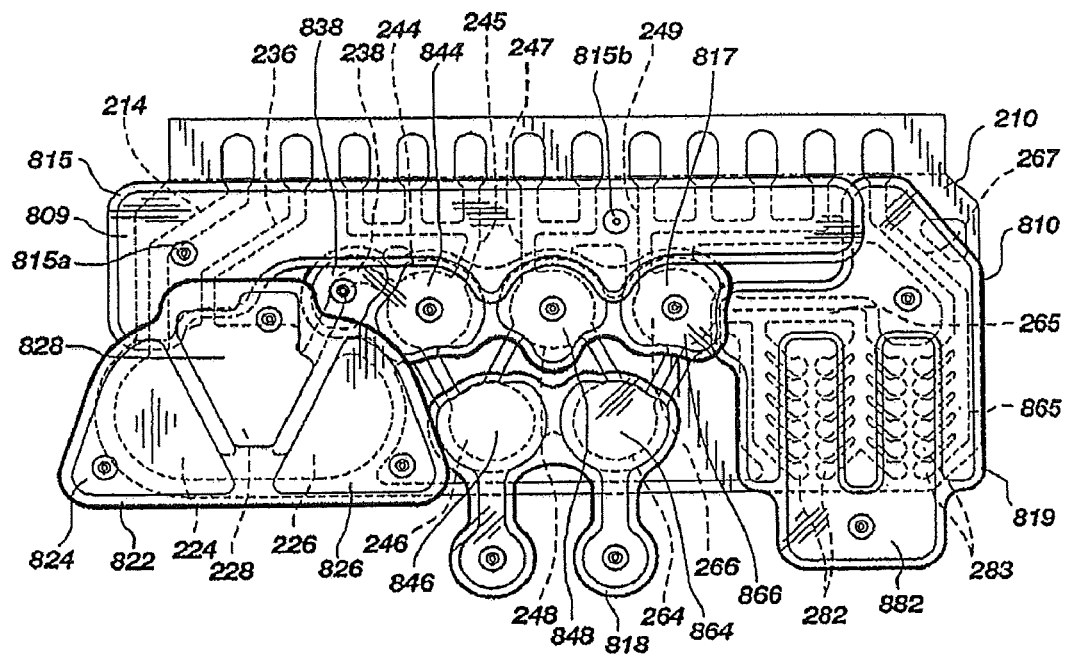
FIG. 9 shows a partial cross-sectional view of the instrument of FIG. 8, including the bladder components of FIG. 7, with the pouch of FIG. 6 shown in shadow.

FIG. 9 shows the relationship between bladder assembly 810 and pouch 210 during operation of instrument 800. Bladder assembly comprises sub-assemblies 815, 817, 818, 819, and 822. Because bladder 809 of bladder sub-assembly 815 is large, bladder sub-assembly 815 illustratively has two pneumatic fittings 815a and 815b. Bladder 809 is used to close off chambers 292 (as shown in FIG. 6) from the plastic film portion 217 of pouch 210. When one of the plungers 268 is depressed, one or both of pneumatic fittings 815a and 815*b* permit bladder 809 to deflate. After the fluid from one of the chambers 292 passes through, bladder 809 is re-pressurized, sealing off channels 214, 236, 245, 247, and 249. While illustrative bladder sub-assembly 815 has only one bladder 809, it is understood that other configurations are possible, illustratively where each of channels 214, 236, 245, 247, and 249 has its own associated bladder or pneumatic piston. Bladder sub-assembly 822 illustratively comprises three bladders 824, 826, and 828. As discussed above, bladders 824, 824, and 828 drive the three-lobed blister 222 for cell lysis. As illustrated, bladders 824, 826, and 828 are slightly larger than their corresponding blisters 224, 226, 228. It has been found that, upon inflation, the surface of the bladders can become somewhat dome-shaped, and using slightly oversized bladders allows for good contact over the entire surface of the corresponding blister, enabling more uniform pressure and better evacuation of the blister. However, in some circumstances, complete evacuation of individual blisters may or may not be desired, and larger or smaller-sized bladders may be used to control the blister volume evacuated. Bladder sub-assembly 817 has four bladders. Bladder 836 functions as a pinch-valve for channel 236, while bladders 844, 848, and 866 are configured to provide pressure on blisters 244, 248, and 266, respectively. Bladder sub-assembly 818 has two bladders 846 and 864, which are configured to provide pressure on blisters 246 and 264, respectively. Finally, bladder sub-assembly 819 controls second-stage amplification zone 280. Bladder 865 acts as a pinch valve for channels 265 and 267, while bladder 882 provides gentle pressure to second-stage blisters 282 and 283, to force second-stage blisters into close contact with heater 888. While bladder assembly 810 is provided with five sub-assemblies, it is understood that this configuration is illustrative only and that any number of sub-assemblies could be used or that bladder assembly 810 could be provided as a single integral assembly.

Figure 10:
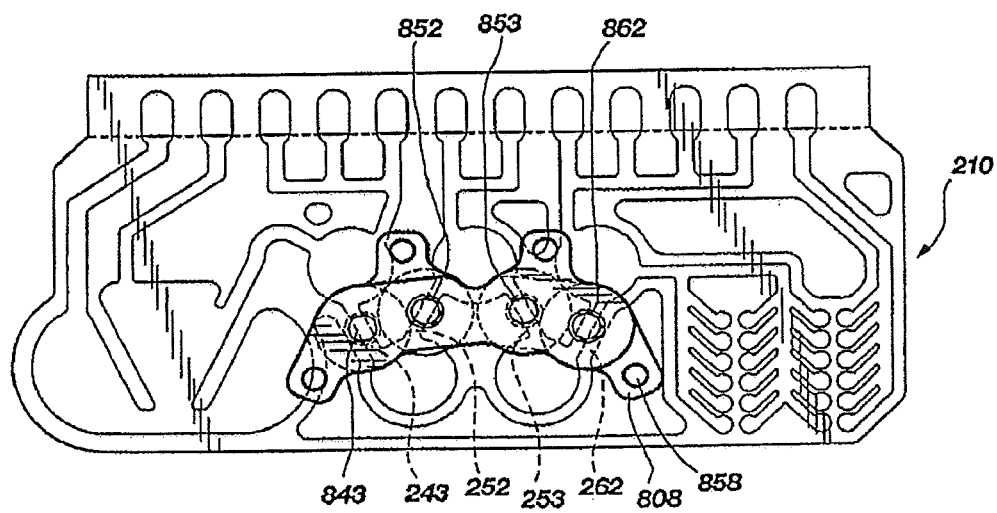
FIG. 10 shows a partial cross-sectional view of the instrument of FIG. 8, including various bladders for pinch valves and the pouch of FIG. 6.

FIG. 10 similarly shows the relationship between pneumatic valve assembly 808 and pouch 210 during operation of instrument 800. Rather than bladders, pneumatic valve assembly 808 has four pneumatic pistons 842, 852, 853, and 862. These pneumatic pistons 842, 852, 853, and 862, each driven by compressed air, provide directed pressure on channels 242, 252, 253, and 262. Because the pistons are fairly narrow in diameter, they can fit between bladder sub-assembly 817 and bladder sub-assembly 818 to provide pinch valves for channels 242, 252, 253, and 262, allowing channels 242, 252, 253, and 262 to be fairly short. However, if desired, pneumatic pistons 842, 852, 853, and 862 could be replaced by bladders, which may be included in bladder assembly 810, obviating the need for pneumatic valve assembly 808. It is understood that any combination of bladders and pneumatic pistons are within the scope of this invention. It is also understood that other methods of providing pressure on the channels and blisters of pouch 210, as are known in the art, are within the scope of this invention.

FIG. 12 shows a pouch 510 that is similar to pouch 210 of FIG. 6. Fitment 590, with entry channels 515*a* through 515*l*, is similar to fitment 290, with entry channels 215*a* through 215*l*. Blisters 544, 546, 548, 564, and 566, with their respective channels 538, 543, 552, 553, 562, and 565 are similar to blisters 244, 246, 248, 264, and 266, with their respective channels 238, 243, 252, 253, 262, and 265 of pouch 210. The channels 245, 247, and 249 of pouch 210 have been somewhat reconfigured as channels 545*a-c*, 547*a-b*, and 548*a-c* on pouch 510; the respective channels of 510 are somewhat shorter than their counterpart channels on pouch 210. However, it is understood that channel configurations are illustrative only, and that various channel configurations are within the scope of this invention.

There are two main differences between pouch 510 of FIG. 12 and pouch 210 of FIG. 6. First, three-lobed blister 222 has been replaced by lysis blister 522. Lysis blister 522 is configured for vortexing via impaction using rotating blades or paddles 21 attached to electric motor 19, as shown in FIG. 2*b*. Since this method of lysing does not rely on alternating pressure of pneumatic pistons, only a single-lobed blister is shown. Because lysis blister 522 has only a single lobe, both channels 514 and 536 lead to the single lobe of lysis blister 522. It is understood that lysis blister 522 may be used in any of the pouch embodiments described herein. It is further understood that lysis assembly 810 illustratively may be modified to replace bladders 824, 826, and 828 of bladder sub-assembly 822 with a single bladder configured for blister 522. Conversely, a three-lobed blister, as described in various other embodiments above, may be used in pouch 510. Lysis blister 522 may be provided with an optional reinforcing patch 523, illustratively attached using adhesive or lamination to the exterior surface of lysis blister 522. Reinforcing patch 523 aids in minimizing tearing of pouch 510 due to repeated contact by paddles 21. FIG. 13 shows an electric motor, illustratively a Mabuchi RC-280SA-2865 DC Motor (Chiba, Japan), mounted on second support member 804. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 21 are impacting pouch 510. Other voltages and speeds may be used for lysis depending on the motor and paddles used. Optionally, controlled small volumes of air may be provided into the bladder adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis.

The second main difference between pouch 510 of FIG. 12 and pouch 210 of FIG. 6 is that the blisters 281, 282, and 283 of second-stage amplification zone 280 have been replaced by high density array 581 in second-stage amplification zone 580. High density array 581 comprises a plurality of second-stage wells 582, illustratively 50 or more wells, and even more illustratively 120 or more wells. Embodiments with more second-stage wells 582, illustratively about 200, about 400, or even about 500 or more are within the scope of this invention. Other configurations are within the scope of this invention as well. Additional second-stage wells 582 may be added by making wells 582 smaller, by making high density array 581 larger, or a combination thereof. For second-stage PCR, each of the wells may contain a pair of primers. It is understood that one or more wells may be used for positive or negative controls.

Cross-contamination between wells as the wells are filled with the diluted first-stage amplification product in blister 566 can be a major problem. Cross-contamination was controlled in pouch 210 by filling each second-stage blister through a separate branch of channel 265 and then sealing with bladder 882, illustrated in FIG. 9. With high density array 581, wherein fluid may fill some or all of blister 584, cross-contamination between wells must also be controlled. In one embodiment, the second-stage PCR primers may be bound covalently or non-covalently to the inside surface of each well, thus functioning much like a PCR chip. However, in many embodiments it is desirable to control cross-contamination between wells without tethering the PCR primers to the wells. Controlling cross-contamination between wells can be difficult in an embodiment wherein the fluid from blister 566 is moved to wells 582 by flowing across a first surface 581a of high density array 581.

There are several desirable features for successful loading of the second-stage amplification zone 580. First, it is desirable that the incoming fluid from blister 566 fill substantially all of the wells 582 to substantially the same level. An unfilled well would produce a false negative signal. Second, it is desirable that the process of filling the wells 582 should not cause the primers in the well to leak out. Loss of primers from one well can limit the efficiency of the PCR reaction in that well and can contaminate neighboring wells. Third, after the wells 582 have been filled and PCR started, it is desirable that the wells be completely sealed from each other. Amplicon leakage out of one well and into another well can lower signal in the first well and raise signal in the second well, potentially leading to a false negative in the first well and a false positive in the second well. Further, for certain kinds of controls, it is important that amplicon generated in one well not enter another well where it can be further amplified.

Solutions to this problem include use of a barrier layer. In one example, the barrier layer is a physical barrier that is provided to allow for rapid loading of the wells and for rapid sealing from the bulk fluid. In another example, combined chemical and physical barriers are used, wherein the physical barrier is used to seal the wells and then the chemical barrier conditionally releases the oligonucleotide primers into the well solution, for example by heating, slow release, or enzymatic digestion. Well depth or channel length to each well also may be used to control release of the reagents from the wells. Other means for loading high density array 581 are possible.

Figure 14:
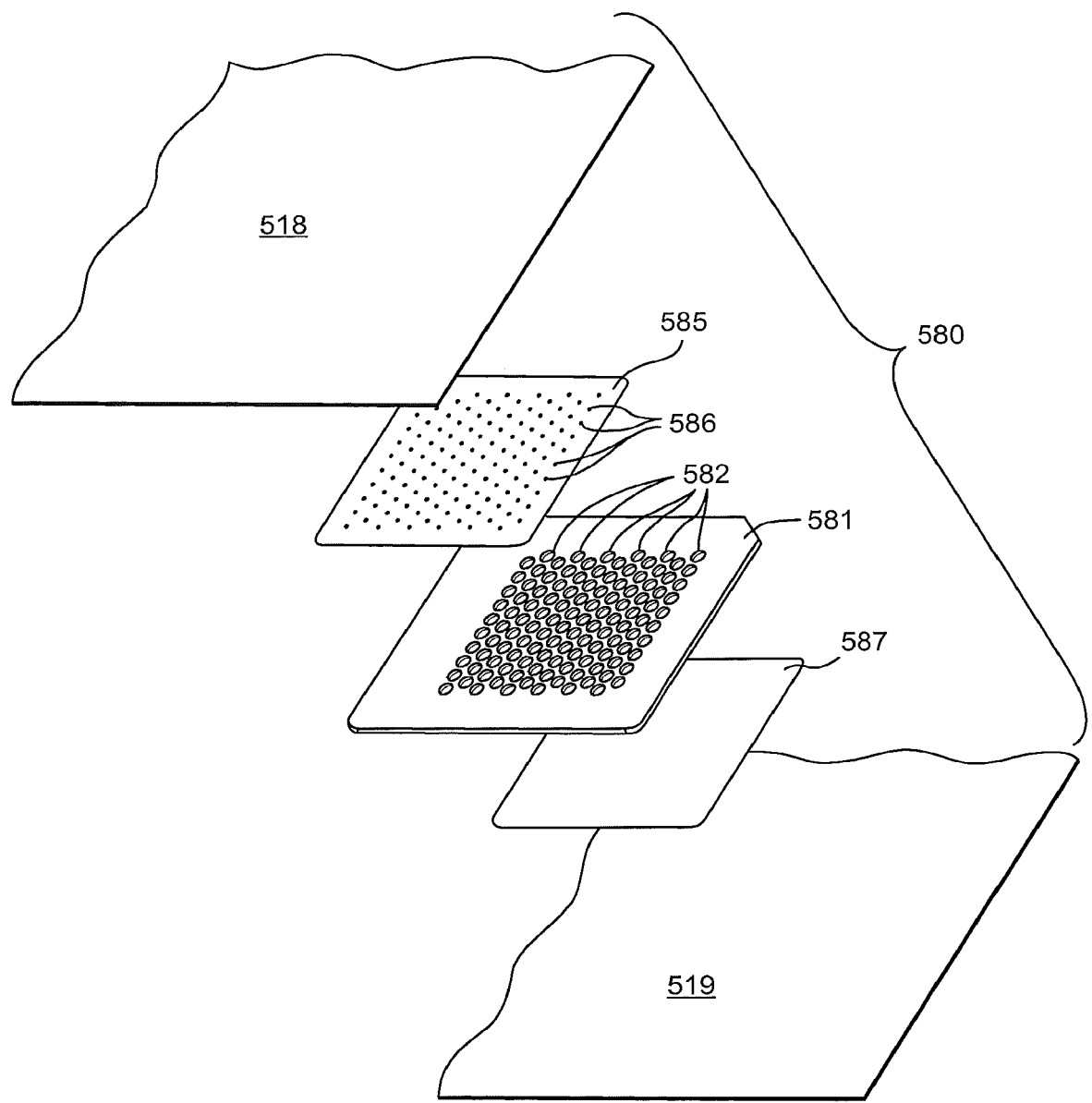
FIG. 14 is an exploded perspective view of the second-stage high density array of FIG. 12.

FIGS. 12-15 show an illustrative embodiment of second-stage 580 using a physical barrier. Sandwiched between first layer 518 and second layer 519 of pouch 510 is high density array 581, with wells 582. As best seen in FIG. 14, pierced layer 585, with piercings 586, is provided on one side of high density array 581 to act as the physical barrier, and a second layer 587 is provided on the opposite side of high density array 581 to form the bottom of wells 582. Illustratively, pierced layer 585 and second layer 587 are plastic films that have been sealed to high density array 581, illustratively by heat sealing, although it is understood that other methods of sealing may be employed. It is also understood that the material used for high density array 581 and the material used for pierced layer 585 and second layer 587 should be compatible with each other, with the sealing method, and with the chemistry being used. When used for PCR, examples of compatible plastics that can used for high density array 581 and can be heat-sealed are PE, PP, Monprene®, and other block copolymer elastomers. If fluorescent dyes are used in the detection chemistry, it may be desirable for high density array 581 to be formed from black or other relatively fluorescently opaque materials, to minimize signal bleed from one well 582 to its neighboring wells and for at least one of layers 585 and 587 to be relatively fluorescently transparent. For pierced layer 585 and second layer 587, laminates of a strong engineering plastic such as Mylar® or PET with heat-sealable plastic layers such as PE, PP and Dupont Surlyn® may be used. For adhesive-based systems, rigid engineering plastics such as PET or polycarbonate may be used to form high density array 581 and films of PCR-compatible plastics are then used as pierced layer 585 and second layer 587. In one illustrative embodiment, high density array 581 is formed of black PE, a composite polyethylene/PET laminate (or Xerox® PN 104702 hot laminating pouch material) is used for pierced layer 585 and second layer 587 which are heat sealed to high density array 581, and composite polypropylene/PET is used for first and second layers 518, 519 of pouch 510.

It is understood that piercings 586 align with wells 582. It is also understood that piercings 586 are small enough that, absent some force, fluid does not readily flow through piercings 586. Illustrative piercings may be 0.001-0.1 mm, more illustratively 0.005-0.02 mm, and more illustratively about 0.01 mm. In the illustrative embodiment, second-stage amplification zone 580 is provided under vacuum, such that when fluid is received from blister 566, the vacuum draws fluid through piercings 586 into each well 582. Once the wells 582 are filled, a force is no longer present to force fluid into or out of the wells 582. A bladder adjacent second-stage amplification zone 580 (not shown, but similar in position to bladders 880/882) may then be activated to press first layer 518 against high density array 581 and seal fluid into the wells 582. While first layer 518 of pouch 510 is used to seal the wells 582, it is understood that an optional sealing layer may be provided between pierced layer 585 and first layer 510.

Figure 15:
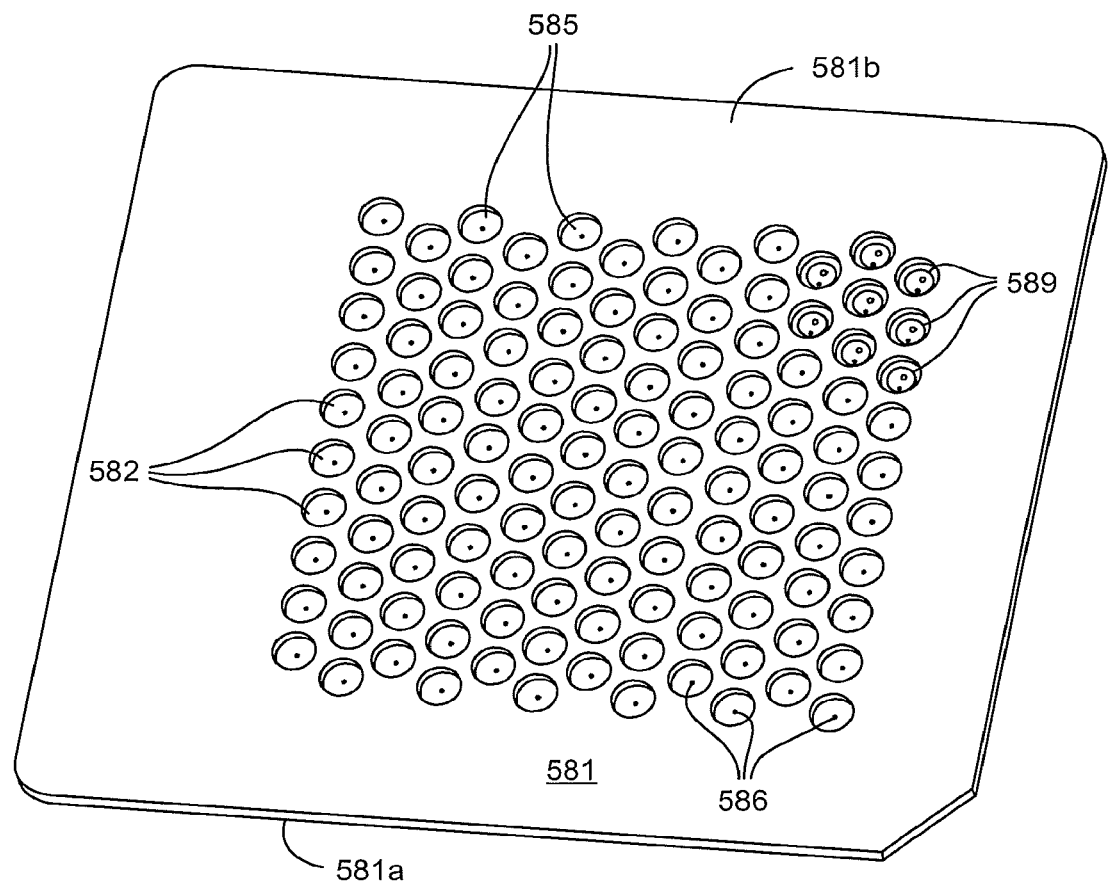
FIG. 15 is a bottom view of the second-stage high density array of FIG. 12, shown during construction of the second-stage high density array.

In one illustrative example, second-stage amplification zone 580 may be prepared as follows. High density array 581 may be prepared by first punching, molding, or otherwise forming an array of wells 582 in a plastic sheet (illustratively 0.1 to 1 mm thick). The wells may form any regular or irregular array that is desired, and may have a volume illustratively of 0.05 µl to 20 µl, and more illustratively of 0.1 µl to 4 µl. One of layers 585 or 587 is then laminated to a first surface 581a of high density array 581, illustratively by heat or adhesive. As shown in FIG. 15, pierced layer 585 is applied to first surface 581a. Reagents 589, illustratively elements of the chemistry of the array that are unique, such as PCR primer pairs, are then spotted into the wells either manually by pipetting, or automatically (illustratively using x/y positionable spotters such as pin-spotters, dot-matrix printers, small-volume automatic pipettes, or micro-fluidic micro-contact spotters). After the reagents 589 have been dried in each well 582, the second of layers 585 or 587 is applied to the second surface 581b of array 581. Layer 585 is pierced using an array of small diameter needles to form piercings 586. Piercings 586 may be formed either before or after layer 585 has been fixed to array 581. It is understood that spotting can be done on either layer 585 before or after piercing or on layer 587. Spotting an array with holes pre-pierced has not shown to leak substantially and offers the advantage that the needles used for piercing are not contaminated by touching the spotted reagents. Alternatively, to minimize the possibility of leakage, and to position the spotted reagents at the most distant location in the array, it may be desirable to spot the reagents 589 onto second layer 587, seal the array 581 with layer 585, and then pierce layer 585. In an illustrative example, reagents are spotted onto second layer 587 using a GeSiM A060-324 Nano-Plotter 2.1/E (Grosserkmannsdorf, Germany). Using such a spotter, multiple arrays may be spotted simultaneously.

Once spotted and pierced, array 581 is placed inside layers 518 and 519 of pouch 510 and sealed in place, illustratively by either heat sealing, using an adhesive, ultrasonically welding, mechanical closure, or other means of enclosing array 581 inside pouch 510 within blister 584. It is understood that blister 584 is fluidly connected to blister 566 via channel 565, and that liquid can flow from channel 565 into blister 584 and over piercings 586. In one illustrative example, when blister 584 is formed, care is taken to allow a path for air to escape. This can be accomplished by "waffling" the inside surface of first layer 518 adjacent to second-stage amplification zone 580 to imprint the film material with a pattern of slightly raised texture. This allows air and liquid to pass along the surface of pierced layer 585, and better allows liquid to reach and fill all of wells 582. The pouch 510 is then placed inside a vacuum chamber and evacuated. Illustratively, when the pressure has reached approximately 0.3 millibars, a pneumatic cylinder inside the vacuum chamber is actuated, driving down a plunger into fitment 590 to seal channel 567, thereby cutting the path from the array inside the sealed pouch, and the vacuum chamber. A plurality of other plungers are also driven into fitment 590 to seal the various entry channels 515. The pouch is removed from the vacuum chamber and may be packaged for long-term storage in a vacuum-bag.

Pouch 510 may be used in a manner similar to pouch 210. Because array 581 is packaged in vacuum, when liquid is moved from blister 566 to second-stage amplification zone 580, the liquid sample is drawn through piercings 586 and into wells 582. Excess liquid is forced away by inflating a pneumatic bladder over the array and thermal cycling is accomplished as described above, illustratively by heating and cooling a Peltier element pressed against one side of the array.

As mentioned above, pierced layer 585 may be replaced by a variety of suitable physical or chemical barriers. In one illustrative embodiment using a chemical barrier, pierced layer 585 is omitted, and reagents 589 are spotted into wells 582 in a buffer that dissolves relatively slowly. Illustratively, reagents 589 that contain polymers such as PEG, Ficoll or polysorbate 20 or sugars such as sucrose, trehalose or mannitol in appropriate concentrations will be compatible with the second-stage PCR reaction and may dissolve more slowly than primers spotted solely in water or Tris/EDTA. The primers spotted in one of these buffers may be air dried into the wells 582, as described above (it is understood that in such an embodiment, second layer 587 is affixed to high density array 581 for spotting). These same polymers may be used in lyophilization of enzyme reagents (e.g. the enzymes and buffers used in PCR) to form an open matrix containing the stabilized enzymes. Thus, the primers spotted in these buffers can be lyophilized in place in the wells 582, leading to slower but potentially more complete rehydration than with air drying. When pouch 510 is used, the fluid from blister 566 is driven into the well by vacuum or pressure and starts to dissolve the primer mix. By selecting a buffer that dissolves suitably slowly, when the bladder adjacent second-stage amplification zone 580 is actuated, the contents of each well 582 is sealed therein prior to any substantial cross-contamination.

Another embodiment uses a matrix that does not dissolve until second-stage amplification zone 580 is heated above a predetermined temperature. One example of such a matrix is low melt agarose such as GenePure LowMelt Agarose (ISC Bioexpress). In one example, a 1.5% solution of this agarose melts at 65° C. and gels at 24-28° C. Prior to spotting, reagents 589 illustratively may be warmed to 50° C. and mixed with this agarose that had already been melted and then spotted into wells 582 in a small volume (illustratively 100 to 500 nl). To keep the mixture liquid during spotting, this may have to be done in a cabinet heated above the melting temperature of the agarose. Alternatively, it may be possible to pipette dilute solutions of the agarose without melting. After the agarose/reagent mixture is spotted, the high density array 581 is dried. This can be a simple air drying or the primer-agarose mixture can contain the sugars and polymers listed above so that the reagents can be freeze dried. When pouch 510 is used for PCR, second-stage amplification zone 580 may be heated, illustratively to 55° C., as the fluid from blister 566 is moved into high density array 581. At this temperature, the agarose does not melt so the primers are not released into solution. Once high density array 581 is filled, the corresponding bladder is inflated to seal the wells. When the temperature rises above 65° C. in the first denaturation step of the first PCR cycle, the agarose containing the primers melts, releasing the primers into the master mix. Illustratively, thermal cycling never goes below 60° C. (or other melting temperature for the agarose) so that the agarose does not gel during thermal cycling. Furthermore, in the illustrative instrument 800 of FIG. 8, the repeated temperature cycling is driven by heater 888, which is located on one side of the pouch. It is expected that there will often be a temperature gradient across the PCR solution in wells 582, which should facilitate mixing of the primers by convective fluid flow. Wax may also be used in a similar embodiment.

In a further embodiment, the primers may be conditionally bound to the wells 581, with subsequent releasing of the primers into solution after the wells 581 have been filled. Depending upon how the primers are attached to the plastic substrate, the primers may be cleaved using heat (illustratively during the first cycle of the PCR reaction), light (illustratively irradiating through window 847), chemicals (e.g. dithiothreitol together with heat will reduce disulfide bonds that may be used to link primers to the wells), or enzymes (e.g. site specific proteases such at Tissue Plasminogen Activator can be used to cleave the proper peptide linker attaching primers to the substrate).

In yet another embodiment, a DNase may be injected into second-stage amplification zone 580 subsequent to amplification, to minimize further any potential risk of contamination.

It is understood that second-stage amplification zone 580 has been described herein for use with PCR. However, other uses for pouch 510 and second-stage amplification zone 580 are within the scope of this invention. Further, it is understood that second-stage amplification zone 580 may be used with or without nucleic acid extraction and a first stage PCR amplification zone. Finally, it is understood that second-stage amplification zone 580 may be used with any of the pouch embodiments described herein.

Example 1: Nested Multiplex PCR

A set of reactions was run in a pouch 110 of FIG. 5, on an instrument similar to instrument 800 but configured for pouch 110. To show cell lysis and effectiveness of the two-stage nucleic acid amplification, 50 µL each of a live culture of S. cerevisaie and S. pombe at log phase was mixed with 100 µL of a nasopharyngeal aspirate sample from a healthy donor to form the sample, then mixed with 200 µL lysis buffer (6M guanidine-HCl, 15% TritonX 100, 3M sodium acetate. 300 µL of the 400 µL sample in lysis buffer was then injected into chamber 192a of pouch 110.

The pouch 110 was manufactured with 0.25 g ZS beads sealed in three-lobed blister 122. Second-stage primers, as discussed below, were also spotted in blisters 181 and 182 during manufacture of pouch 110. The pouch 110 was loaded as follows:

115*a* sample and lysis buffer, as described above,
115*b* magnetic beads in the lysis buffer,
115*d-e* wash buffer (10 mM sodium citrate),
115*g* elution buffer (10 mM Tris, 0.1 mM EDTA)
115*h* first-stage PCR buffer:
    0.2 mM dNTPs
    0.3 µM each primer:
        Sc1: primers configured for amplifying a portion of the YRA1 nuclear protein that binds to RNA and to MEX67p of *S. cerevisaie*. The primers are configured to amplify across an intron such that amplification of cDNA (mRNA reverse-transcribed via M-MLV) yields a 180 bp amplicon.
        Sc2: primers configured for amplifying a 121 bp region of the cDNA of MRK1 glycogen synthase kinase 3 (GSK-3) homolog of *S. cerevisaie*.
        Sc3: primers configured for amplifying a 213 bp region of the cDNA of RUB1 ubiquitin-like protein of *S. cerevisaie*.
        Sp1: primers configured for amplifying a 200 bp region of the cDNA of sucl-cyclin-dependent protein kinase regulatory subunit of *S. pombe*.
        Sp2: primers configured for amplifying a 180 bp region of the cDNA of sec14-cytosolic factor family of *S. pombe*.
    PCR buffer with 3 mM $MgCl_2$ (without BSA)
    50 units M-MLV
    4.5 units Taq:Antibody
    100 units RNAseOut
115*j-k* second-stage PCR buffer
    0.2 mM dNTPs
    1× LC Green® Plus (Idaho Technology)
    PCR buffer with 2 mM $MgCl_2$ (with BSA),
    4.5 units Taq
115*l* second-stage PCR buffer with a sample of the first-stage amplicons.

During manufacture, second-stage blisters 181 and 182 were spotted with nested second-stage primers. Each blister was spotted with one primer pair in an amount to result in a final concentration of about 0.3 µM once rehydrated with the second-stage PCR buffer. The second-stage nested primers are as follows:

Sc1: primers configured for amplifying an 80 bp fragment of the Sc1 cDNA first-stage amplicon.
    Sc2: primers configured for amplifying a 121 bp fragment of the Sc1 cDNA first-stage amplicon.
    Sc3: primers configured for amplifying a 93 bp portion of the Sc1 cDNA first-stage amplicon.
    Sp1: primers configured for amplifying a 99 bp portion of the Sc1 cDNA first-stage amplicon.
    Sp2: primers configured for amplifying a 96 bp portion of the Sc1 cDNA first-stage amplicon.

There is no overlap between the first-stage and second stage primer pairs for any of the targets. Each pair of primers was spotted into one negative control blister 181 and two second-stage blisters 182, so that each second-stage amplification would be run in duplicate, each duplicate with a negative control.

After loading, activation of the plunger associated with entry channel 115*a* moved the sample to three-lobed blister 122, activation of the plunger associated with entry channel 115*b* moved the magnetic beads to reservoir 101, activation of the plungers associated with entry channels 115*d-e* moved wash buffer to reservoirs 102 and 103, activation of the plunger associated with entry channel 115*g* moved elution buffer to reservoir 104, activation of the plunger associated with entry channel 115*h* moved first-stage PCR buffer to reservoir 105, activation of the plungers associated with entry channels 115*j-k* moved second stage PCR buffer to reservoirs 106 and 107, and activation of the plunger associated with entry channel 115*l* moved the positive control (second-stage PCR buffer with a sample of previously prepared first-stage amplicon) to reservoir 108. In this present example, the plungers associated with entry channels 115*a* and 115*b* were depressed prior to loading the pouch 110 into the instrument. All other plungers were depressed sequentially in the instrument during the run, and fluids were moved to reservoirs 102 through 108 as needed.

Once pouch 110 was placed into the instrument, and beating took place for ten minutes in the presence of ZS beads, as described above. Once cell lysis was complete, reservoir 101 was compressed and nucleic acid binding magnetic beads from reservoir 101 were forced into three-lobed blister 122, where the beads were mixed gently and allowed to incubate for 5 minutes.

The sample-bead mixture was then moved to blister 144, where the magnetic beads were captured via activation of the magnet. Once the magnet was deployed, bladders adjacent blister 144 were pressurized to force fluids back to three-lobed blister 122. The captured beads were then washed as described above, using the wash solution from reservoirs 102 and 103. Following washing, the beads were once again captured in blister 144 via activation of the magnet, and the elution buffer stored in reservoir 104 is moved to blister 144, where, after a 2 minute incubation, the nucleic acids eluted from the beads are then moved to blister 161, as discussed above.

In blister 161, the nucleic acid sample is mixed with first-stage PCR master mix from reservoir 105. The sample is then held at 40° C. for 10 minutes (during which time M-MLV converts mRNA to cDNA), then 94° C. for 2 minutes (to inactivate the M-MLV and remove antibody from taq). Thermal cycling is then 20 cycles of 94° C. for 10 second and 65° C. for 20 seconds.

Subsequent to first-stage amplification, the sample is diluted approximately 100-fold using the second-stage PCR master mix from reservoir 106. The sample is then moved to blisters 182, which were previously spotted with the second-stage primers, as discussed above. Second-stage PCR buffer was moved from reservoir 181 to negative control blisters 181, and the positive control mixture was moved to blisters 183 from reservoir 108. The samples were denatured for 30 seconds at 94° C., then amplified for 45 cycles of 94° C. for 5 seconds and 69° C. for 20 seconds.

Figure 11:
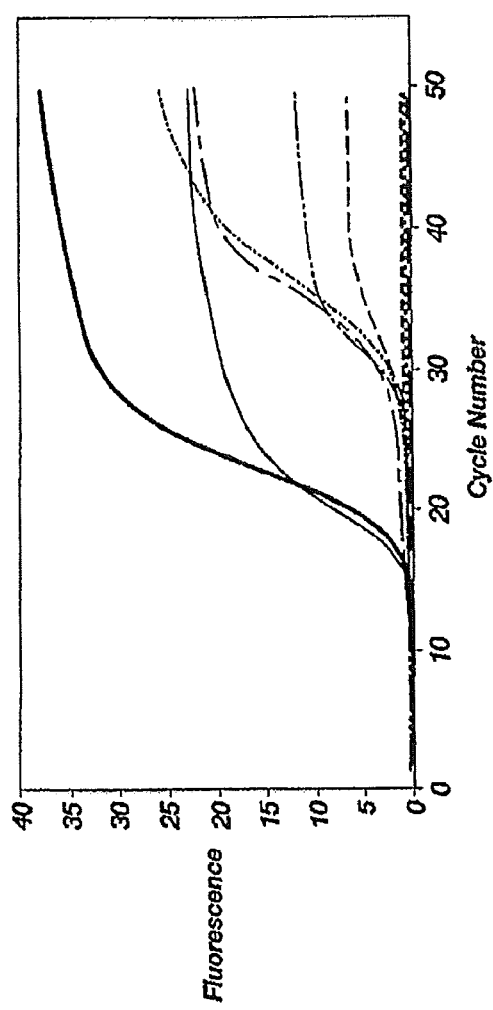
FIG. 11 shows amplification curves from second-stage amplification of a sample that was lysed and amplified in a pouch of FIG. 5 (--- positive control; — — — S. cerevisaie target 1; —— S. cerevisaie target 2; ——— S. cerevisaie target 3; ------ S. pombe target 1; — --— S. pombe target 2; ---- negative controls).

As can be seen in FIG. 11, all target amplicons and the positive control showed amplification, while none of the negative controls showed amplification. Each sample was run in replicates. The replicates each showed similar amplification (data not shown).

It is understood that the *S. cerevisaie* and *S. pombe* targets are illustrative only and that other targets are within the scope of this invention.

Example 2: High Density PCR

The above example uses pouch 110 of FIG. 5. Pouch 110 has five negative control blisters 181, five positive control blisters 183, and ten low volume sample blisters 182. Pouch 210 of FIG. 6 increased the number of low volume sample blisters 282 to 18. However, high density array 581 of pouch 510, shown in FIG. 12 can have 120 or more second-stage wells 582. This increase in the number of second-stage reactions enables a wide set of potential diagnostic and human identification applications without the need to increase the size of the pouch and its instrument. Various examples are described herein.

In one example, it is known that standard commercial immunofluorescence assays for the common respiratory viruses can detect seven viruses: Adenovirus, PIV1, PIV2, PIV3, RSV, Influenza A, and Influenza B. A more complete panel illustratively would include assays for additional five viruses: coronavirus, human metapneumovirus, BOCAvirus, Rhinovirus and non-HRV Enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The illustrative complete respiratory virus panel would also target the SARS coronavirus, possibly the avian influenza HA and N subtypes, and possibly others. Finally, some of the respiratory viruses show such a high rate of sequence variation that it would be beneficial to create more than one nested PCR assay for each such virus, thereby minimizing the chance of false negative results due to sequence variation under the primers. When all of the primer sets described herein are included, such a respiratory virus panel could have 80 or more specific amplicons in the second-stage amplification. The high density array 581 could easily accommodate such a panel in a single pouch 510.

A second application of the high density array 581 of pouch 510 would be to determine the identity and the antibiotic resistance spectrum of the multi-drug resistant bacteria isolated from infected patients. Current methods require several days to culture the organism and empirically test individual drug resistance profiles. During the time it takes to receive the results, physicians will often administer broad-spectrum antibiotics, which leads to an increase in multi-drug resistant bacteria. PCR primers have been developed to detect the genetic determinants of antibiotic resistance (the antibiotic resistance genes themselves). However because of the large number of variants of some of these genes, a large number of amplicons is required for a complete determination of the resistance profile. Hujer et. al. describe a panel of 62 PCR assays to identify the resistance genes present in *Acinetobacter* isolates. Again, the high density array 581 could easily accommodate such a panel in a single pouch.

A third example of the utility of the high density array is in the field of human identification, illustratively for forensic identification of human remains and for paternity testing. Most of the market in human identification is dominated by systems that analyze short tandem repeat sequences (STRs). This analysis has generally required separating the repeats by size, using e.g. capillary electrophoresis. The specialized laboratory equipment used for this purpose has generally not been field portable. There is growing interest in using Single Nucleotide Polymorphisms (SNPs) for identity testing, as there are a large set of techniques for identifying SNPs and some of these are amenable to field use. Sanchez et al. have published a set of 52 well-characterized SNPs that collectively give a very low probability of matching two individuals by chance (a mean match probability of at least $5.0 \times 10^{-19}$). In practice, it may take two amplicons for each SNP to accurately type each locus (see, e.g., Zhou et al.). Thus one pouch 510 with 104 second-stage wells 582 could completely type an individual at all of the 52 SNP loci.

It is understood that there are cost and workflow advantages gained by combining assays from different diagnostic applications into one pouch. For example the complete respiratory virus panel could be combined with the bacterial identification panel. These combinations could simplify manufacturing, since there are fewer types of pouches to assemble. They could also simplify the work of the end user, as there are fewer specific types of pouches that need to be stocked in a clinic, and also reducing the chance of using the wrong pouch for a particular clinical sample. For some applications, these advantages could offset an increase cost of manufacturing the pouch having a greater number of primer pairs. Thus one pouch 510 with 100 or more second-stage wells 582 could be used to accommodate multiple panels of assays.

Example 3: Process Controls

Controls for highly multiplexed assays can be problematic, especially in clinical diagnostic settings where quality must compete with cost per test. The high-density array 582 of pouch 510 potentially increases this problem because of the increased number of diagnostic targets that can be assayed in a single run. Various types of controls are discussed herein.

Illustrative process controls include mixing an intact organism, for example an organism containing an RNA target, into the patient sample before injecting the sample into the pouch. Such a target could be an intact RNA bacteriophage (MS2 or Qβ) or an intact plant RNA virus (Tobacco Mosaic Virus) or an mRNA present in an intact yeast. Outer primers specific for the RNA target would be present in the first-stage PCR and a well 582 containing the inner primers would be present in the high density array. Detection of amplification product in this well 582 confirms that all of the steps of the process are working correctly. A post-second-stage amplification melt curve could also be used to verify that the correct specific product was made. The crossing point ("Cp") determined from an amplification curve could be used to give a quantitative measure of the integrity of the reagents. For example the Cp can be compared to that of other pouches from the same lot run at a different time. While an intact organism is used, it is understood that purified or isolated nucleic acids may be used if it is not important to test for lysis. In other situations, it may be desirable to use the control to test only the later steps of the analysis. For example, spiking a natural or synthetic nucleic acid template into a well in the high density array along with the cognate primers could be used to test the second-stage PCR reaction, and spiking a nucleic acid template into the first-stage PCR with the appropriate primers in the first-stage PCR amplification mixture and in a well 582 of the second-stage amplification zone will test both the first- and second-stage PCR reactions.

Process controls such at described above do not test the integrity of the primers specific to the target amplicons. One example of a positive control that tests the integrity of the specific primers uses a mixture of nucleic acids, illustratively synthetic RNAs, as stability and variability often can be better controlled and these sequences cannot be present due to environmental contamination, wherein the mixture contains a nucleic acid for each of the primers present in the particular pouch. In a diagnostic setting, this positive control could be used at the end of a run of pouches used to test patient samples. The mixture is injected into a pouch, illustratively from the same lot as those used for the patient samples, and success is defined by all of the target amplicons providing a positive result. Negative controls can be done in the same way; at the end of a run of pouches used to test patient samples, water or buffer could be injected into a pouch and success defined by all of the target amplicons providing a negative result.

Individual workflow and protocols in a diagnostic lab may be used to determine the number of patient sample pouches run before the control pouches described above are run. Regardless of how frequently or infrequently the control pouches are run, these controls add to the time and cost of the total system. For this reason, it would be useful to make the controls internal to the pouch. The structure of the high density array 581 allows for the following novel approach to negative controls. In this example, a nucleic acid, illustratively a synthetic amplicon, is spiked into one of the wells 582*a* of the high density array 581. Primers to amplify this sequence are spiked into this well 582*a* and into two other wells 582*b* and 582*c* spaced across the array. Illustratively, the amplicon sequence and primers are artificial and designed so that none of the primers used will amplify another target by chance.

When a clean, uncontaminated pouch 510 is run in instrument 800, the well 582*a* containing the synthetic target will generate amplicon and therefore be called positive. The two other wells 582*a*, 582*b* that contain the corresponding primers should not amplify anything in the sample and thus be called negative. Pouch 510 may be treated further, for additional controls. Illustratively, bladder 880/882 holding the high density array against heater 888 is then depressurized and the contents of the wells 582 are mixed. In one illustrative method, the contents of the wells 582 are mixed as follows: heater 888 is used to cycle the temperature of the high density array above and below the boiling point of the buffer for a short time (for example three cycles of 85° C. for 10 sec then 105° C. for to 20 sec). Bubbles of steam generated in the wells 582 of high density array 581 should force the contents of wells 582 out into the second-stage amplification zone blister 580. Optionally, the contents of the second-stage amplification zone 580 may be mixed with the contents of rest of the pouch 510 by using the bladders to move liquid from one end of the pouch 510 to the other. The purpose of these steps is to mix the specific contamination control amplicon, along with any specific target amplicons throughout the pouch.

If the user accidentally opens a pouch after it has been run in this fashion, then both specific target amplicons and the contamination control amplicon will be released. If trace amounts of these nucleic acids contaminate a later pouch run, the instrument may detect the contamination event, as the wells 582*b*, 582*c* that contained only the primers specific for the synthetic amplicon will score positive. Software in the instrument will alert the user and the results of the run will be flagged as suspect.

In another method to control contamination, at the end of a run, a DNA degrading chemical or enzyme may be added to destroy substantially all of the DNA products of the first- and second-stage PCR reactions. Illustratively, this can be done in a way similar to the contamination detection method described above, by heating the contents of the second-stage array to above the local boiling temperature, thus drawing the amplified sample out of the wells 582 of the array 851, mixing the heated liquid with the diluted contents of the 1$^{st}$ stage reaction, adding an aliquot of a DNA degrading substance, illustratively through entry channel 515*k*, either with or without cooling the mixture, and allowing the DNA degrading reaction to incubate until substantially all of the DNA produced in the PCR reaction has been destroyed. This can be accomplished using DNAases, acids, or oxidants, as are known in the art.

It is understood that any of the contamination controls described herein may be used independently or in any combination thereof.

Example 4: Pouch Loading

Figure 16:
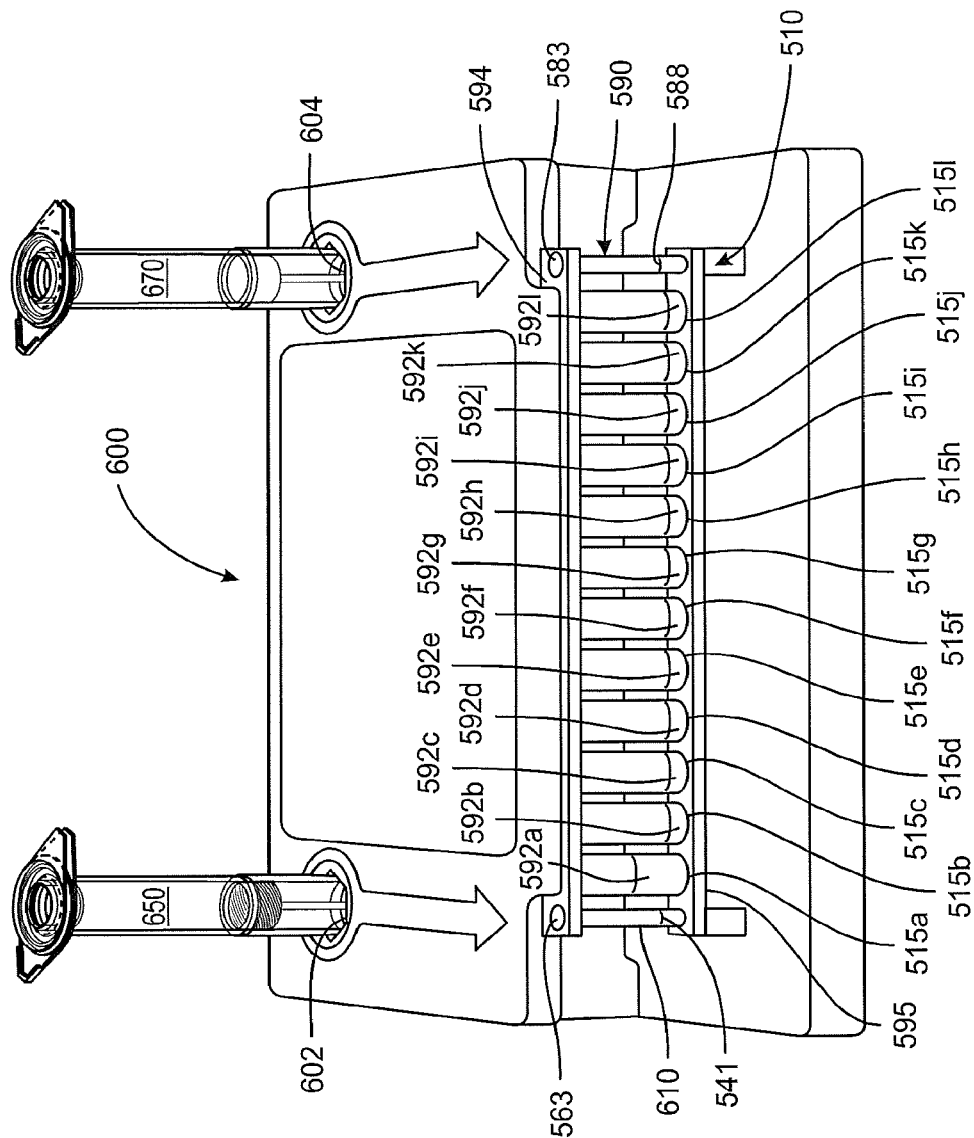
FIG. 16 shows a loading station for loading the pouch of FIG. 12, including the pouch of FIG. 12.

FIG. 16 shows a loading station 600. As shown, pouch 510 of FIG. 12 has been loaded into slot 610 of loading station 600, such that only fitment 590 of pouch 510 is visible. As shown, loading station 600 is provided with a sample vial receptacle 602 for holding sample vial 650 and hydration vial receptacle 604 for holding hydration vial 670. However, it is understood that the receptacles and vials are for aiding workflow and are illustrative only. Other configurations and use with other pouches and other devices are within the scope of this disclosure.

A sample is pipetted or otherwise loaded into sample vial 650. As discussed in more detail below, depending on work flow, sample vial 650 may already contain a buffer or other fluid 652 for receiving the biological sample, or the operator may add the biological sample in an appropriate buffer to sample vial 650. Optionally, the buffer may be provided in a separate ampoule, with an appropriate amount of buffer apportioned. Similarly, hydration vial 670 may be preloaded with water, buffer, or other fluid 672, or the operator may load hydration vial 670 with such fluid.

Illustrative fitment 590 includes an injection port 541 illustratively formed near second surface 595 of fitment 590. As shown, injection port 541 is located in sample injection opening 563, which is configured to receive a cannulated transfer vessel through first surface 594 of fitment 590, such as a cannulated syringe. In this illustrative configuration, injection port 541 is protected from accidental puncture and is not opened until a cannulated transfer vessel is placed into sample injection opening 563. Similarly, illustrative fitment 590 includes a second injection port 588 illustratively formed near second surface 595 of fitment 590, and is located in hydration fluid injection opening 583, which is configured similarly to sample injection opening 563. As configured in this illustrative embodiment, injection port 541 is for receiving the sample to be tested, which sample will be moved to chamber 592*a* or directly into lysis blister 522 (FIG. 12), and second injection port 588 is configured for receiving the hydration fluid 672 (displayed in FIG. 18), such as water or buffer, which hydration fluid 672 will be moved to chambers 592*b* through 592*l*, for subsequent movement through entry channels 515*b* through 515*l*. It is understood that the arrangement of injection ports 541 and 588 and openings 563 and 583 is illustrative and that other configurations are within the scope of this disclosure.

Figure 17A:
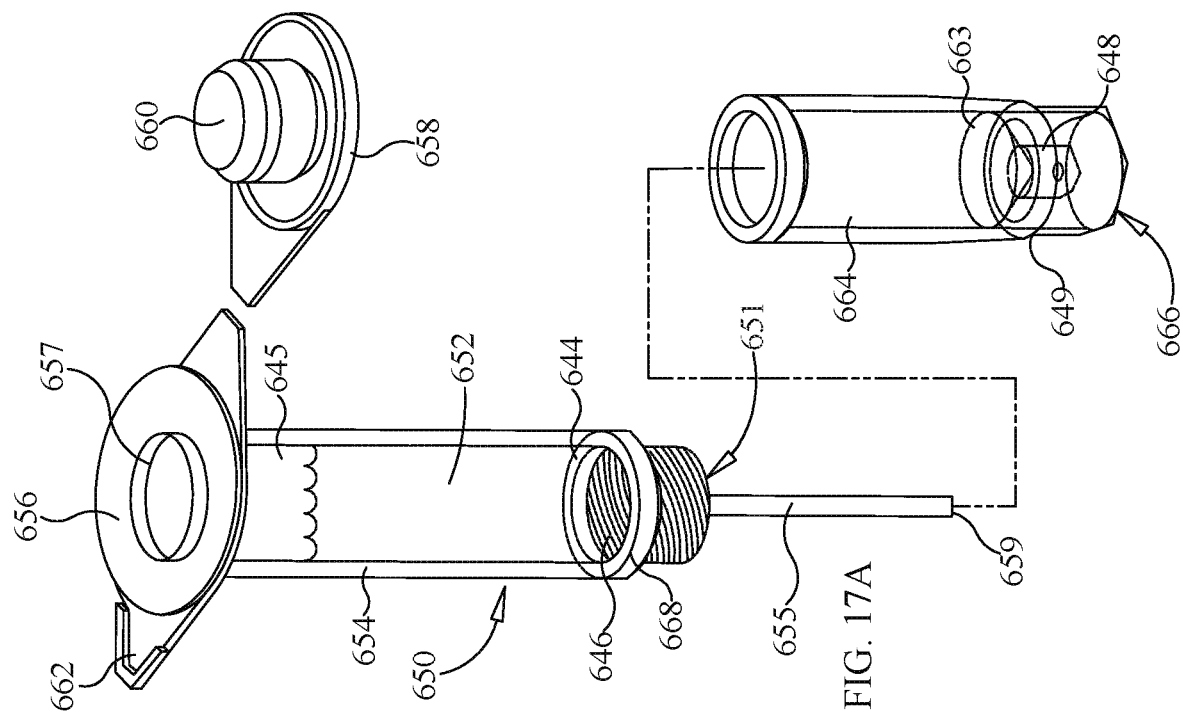
FIG. 17a shows an exploded view of the loading vial of FIG. 17.

Illustrative sample vial 650, as best shown in FIG. 17, is comprised of a top surface 662, a vial body 654, and a cannula 655 extending away from a bottom surface 651 of the exterior of the vial body 654, in an arrangement similar to many cannulated syringes. In this illustrative embodiment, rather than the plunger found in many cannulated syringes, sample vial 650 is provided with a seal 656 affixed to top surface 662 and a cap 658 for extending through top surface 662 for sealing body 654. In the illustrative embodiment, seal 656 is a peelable seal that can be peeled off by the operator. However, it is understood that the seal can be of a variety of different configurations, for example a screw cap or a frangible seal, as are known in the art. Alternatively, a separate seal may be omitted, and sample vial 650 may be provided with cap 658 closing vial body 654, thereby requiring the operator to open cap 658 prior to use. Additionally, a seal of any type is only required if sample vial 650 is provided pre-loaded with sample buffer or other fluid 652, or if vial body 654 needs to remain sealed from an outside environment prior to use, such as to maintain sterility. In an alternative embodiment, sample vial may be provided empty, without seal 656, and the operator would pour, pipette, insert swab, scoop solid or semi-solid material, or otherwise transfer a fluid and/or other materials through opening 657 in top surface 662 and into vial body 654.

Depending on the type of sample to be tested, sample vial 650 may be provided with a filter 646, illustratively located at or near the bottom surface 668 of vial body 654. As shown, filter 646 is held in place by o-ring 644. However, it is understood that filter 646 may be held in place by adhesive, by welding, by being press-fit into place, or by other means, as are known in the art. When cannula 655 is inserted into sample injection opening 653 and the sample is drawn into pouch 510, the sample material is filtered as it is pulled through filter 646 and into cannula 655. While the selection of filter material depends on the sample type and particle size, suitable filters for various biological samples include Pall 100 µm Absolute Ultipleat Polypropylene Melt Blown Media and Millipore 80 µm Polypropylene Net Filter. Most syringe filters are designed to exclude organisms of a certain size, thereby removing those organisms from the filtrate. Unlike such pre-existing filters, these illustrative filters were chosen based on their ability to exclude larger particulates found in stool, soil, powder, etc., while allowing target organisms (e.g., bacterial, viral, protozoan and fungal organisms) of approximately 60 µm in diameter or less to pass through in the filter. Also, the illustrative filter material is inert (i.e. does not bind organism or nucleic acid) and is relatively resistant to clogging. It is understood that these illustrative filters were chosen for samples that include protozoans as target organisms (up to about 60 µm). Because some pouch configurations may test only for smaller targets, filters with a smaller pore size may be desired, such as filters with pore sizes of 1-10 µm for bacteria and fungi, and pore sizes of less than 1 µm if only viral particles are to be detected. Of course, the larger pore size filter can still be used to filter smaller targets. Such filters may be particularly useful for sample types that have a large amount of particulate matter, such as soil, stool, and powder that may clog the fluid system. Further, it is understood that the pore size is chosen based on the materials to be filtered, and that other pore sizes are within the scope of this invention.

As shown, bottom cap 664 is provided with a hexagonal portion 666, which is configured to fit into the hexagonally shaped sample vial receptacle 602. While portion 666 and sample vial receptacle are hexagonal in the illustrative embodiment, it is understood that other shapes may be used, and that the hexagonal or other mating or interlocking shapes may be provided to assist the operator in removing bottom cap 664. Alternatively, the operator may remove bottom cap 664 by other means, such as using two hands to twist bottom cap 664 from vial body 654. Bottom cap 664 may be press-fit on, threaded onto, or otherwise affixed to vial body 654.

In the illustrative embodiment, bottom cap 664 is provided with a seat 648, whereby a bottom end 659 of cannula 655 extends into seat 648. Illustratively, bottom end 659 of cannula 655 fits tightly into seat 648, such that seat 648 provides an airtight seal around the open bottom end 659 of cannula 655. Optionally, vents 649 are provided between bottom cap 664 and vial body 654.

Figure 18A:
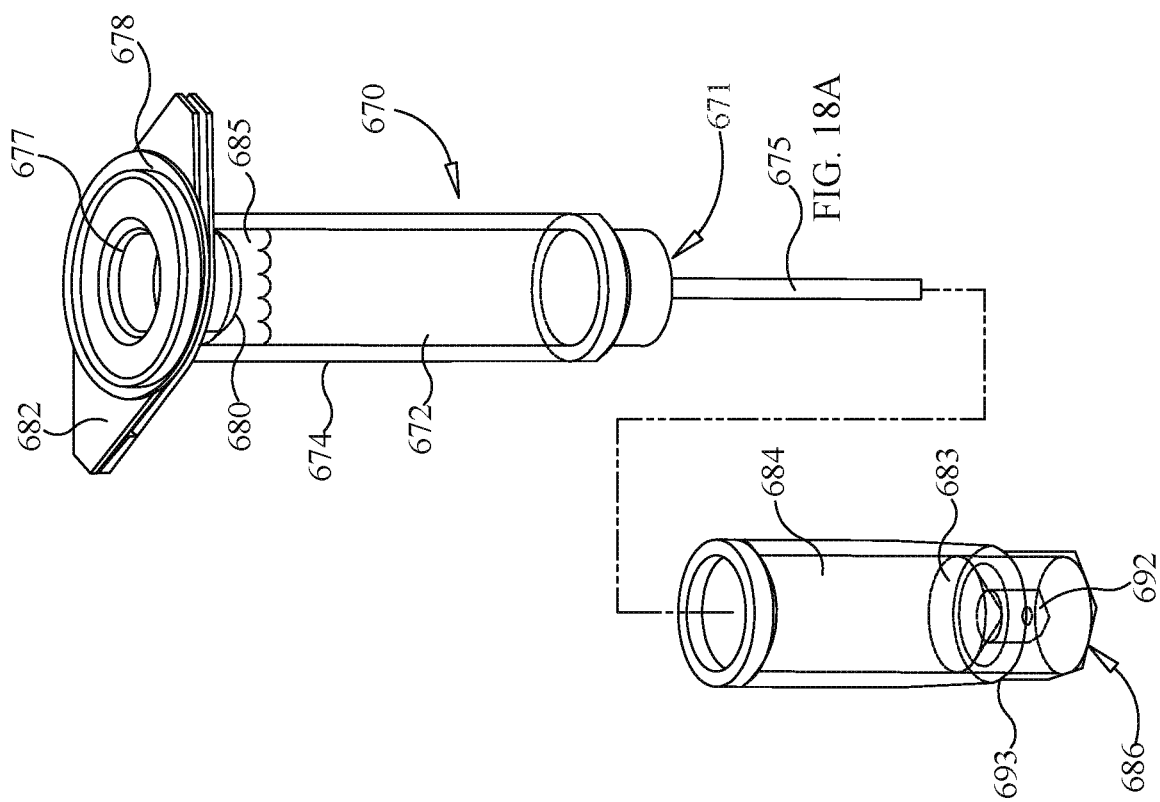
FIG. 18a shows an exploded view of the hydration vial of FIG. 18.

Turning now to FIG. 18, hydration vial 670 may be configured similarly to sample vial 650. However, it may be desirable to preload hydration vial 670 with hydration fluid 672 and pre-seal the hydration fluid 672 in hydration vial 670, as shown in FIG. 18. Illustrative sample vial 670, as shown in FIG. 18, is comprised of a top surface 682, a vial body 674, and a cannula 675 extending away from a bottom surface 671 of the exterior of the vial body 674, in an arrangement similar to that of sample vial 650. However, tongue 680 of cap 678 of illustrative hydration vial 670 is already press-fit into opening 677 of top surface 682, and cap 678 may be sealed to top surface 682, thereby preventing opening of hydration vial 670. This arrangement is illustrative only, and it is understood that other ways of sealing hydration fluid 672 within hydration vial 670 are envisioned herein. Illustratively, vial body 674 and cannula 675 may be provided completely full or essentially completely full of fluid 672, so that handling or rotating hydration vial 670 will not permit air to enter cannula 675. Alternatively, some air 685 or other gas may be present within vial body 674, and the operator may maintain vial body 674 in an upright position to prevent air from entering cannula 675. In yet another alternative embodiment, the air 685 may be provided under pressure, and removal of bottom cap 684 would result in hydration fluid 672 being forced through cannula 675. As shown, hydration vial 670 is not provided with a filter, although one may be provided, if desired.

Bottom cap 684 may be provided to retain any fluid that might drip from cannula 675, as well as preventing contamination of hydration fluid 672 in cannula 675. A wiper 683 may be provided in bottom cap 684 to wipe excess fluid from the bottom of cannula 675. The conical shape of wiper 683 may also aid in retaining drips in bottom cap 684 during subsequent handling and disposal. In the illustrative embodiment, bottom cap 684 is provided with a hexagonal portion 686 for mating with the hexagonally shaped hydration vial receptacle 604, although other shapes are possible, as discussed above with respect to sample vial 650. Hexagonal portion 686 of hydration vial 670 and hexagonally shaped hydration vial receptacle 604 may be of different dimensions and/or different shapes than hexagonal portion 666 of sample vial 650 and hexagonally shaped sample vial receptacle 602, such that only sample vial 650 will readily fit into sample vial receptacle 602 and only hydration vial 670 will readily fit into hydration vial receptacle 604, to reduce the chance of the operator confusing the sample vial 650 and hydration vial 670, so that the proper fluids are injected through ports 541 and 588. In addition, sample vial 650 and injection opening 563 may be partially or entirely provided in a matching specific color, illustratively red, while hydration vial 670 and injection opening 583 may be partially or entirely provided in a different matching specific color, illustratively blue, to provide the operator with visual assistance in providing the proper fluids in ports 541 and 588. To further minimize risk of inserting the wrong liquid into the wrong injection opening, the diameter of cannula 655 may differ from the diameter of cannula 675, and the diameters of sample injection opening 563 and hydration fluid injection opening 583 may similarly differ. Other configurations are within the scope of this disclosure.

Illustratively, to load pouch 510, the operator would place sample vial 650 into sample vial receptacle 602 and hydration vial 670 into hydration vial receptacle 604 on loading station 600. Pouch 510 would also be placed into slot 610.

The operator would remove seal 656 and place the sample into the sample buffer in vial body 654, as directed. The sample would be placed into the sample buffer in any way suitable for the sample type, including inserting a swab, pipetting a fluid sample, dripping blood from a patient directly into the vial body, and placing a solid or semi-solid sample such as stool into the vial body, with optional vortexing or other mixing, as is standard in the art. Depending on the sample type and desired target nucleic acids, the sample buffer may contain one or more additives or stabilizers, such as proteases, RNAses, RNAse inhibitors, and the like. Additionally or alternatively, these additives may be provided in the pouch 510. Preferably before vortexing or mixing, the operator would close sample vial 650 by placing the tongue 660 of cap 658 through opening 657. Inserting tongue 660 pressurizes the air contained within vial body 654. Illustratively, tongue 660 has a volume equal to or greater than the volume of cannula 655. Illustratively, when bottom cap 664 is removed, the airtight seal between seat 648 bottom end 659 of cannula 655 is broken, and substantially all air is forced out of cannula 655. If the volume of tongue 660 is greater than the volume of cannula 655, such would help ensure that the maximal amount of air is displaced from cannula 655. Any overflow in the amount of fluid forced into and potentially through cannula 655 can be captured in bottom cap 664 and removed from the bottom of cannula 655 by wiper 663. By completely or essentially completely filling cannula 655, the quantity of bubbles in pouch 510 upon loading of the pouch is minimized. One or more vents 649 may aid in separation of bottom cap 664 from hydration vial 650.

Because bottom cap 664 is provided with a hexagonal portion 666, which is configured to fit into the hexagonally shaped sample vial receptacle 602, the operator can easily twist off bottom cap 654 while bottom cap is engaging receptacle 602, thereby exposing cannula 655. Cannula 655 is then inserted into sample injection opening 563 and is pushed in, opening injection port 541. A vacuum inside pouch 590 (or reduced pressure inside the pouch relative to atmospheric pressure or pressure outside the pouch) illustratively forces the sample through the filter (if present), with or without pressure from the vial body, may be used to draw the sample into pouch 510, illustratively into chamber 592a in fitment 590, for subsequent movement into lysis chamber 522. By assuring that cannula 655 is substantially filled with fluid 652, the amount of air or other gas moved from sample vial 650 into pouch 510 is minimized, thereby minimizing the size and quantity of bubbles. Furthermore, when a prior art syringe with a plunger is used and the vacuum inside pouch 590 draws fluid, the plunger is drawn down the syringe, thereby equilibrating the pressure inside the syringe. In the embodiment of FIGS. 16-17, because the opening at the top of each of the vial bodies is sealed, when the vacuum from inside pouch 590 draws fluid from the vial, the vial will also experience negative pressure and may degas the sample and draw some remaining air bubbles out of the pouch 590. Cannula 655 is then withdrawn from sample injection opening 563 and sample vial 650 and bottom cap 664 are disposed of according to protocols. Since the vial body is under negative pressure, as cannula 655 is withdrawn, air bubbles that may have collected near injection port 541 may be drawn out of pouch 510, further reducing air bubbles in the pouch.

Similarly, the operator twists off bottom cap 684 from hydration vial 670, thereby exposing cannula 675. If the contents of hydration vial 670 are provided under pressure, a small amount of hydration fluid may leak out into bottom cap 684 when cannula 675 is separated from seat 692. One or more vents 693 may aid in separation of bottom cap 684 from hydration vial 670. Cannula 675 is then inserted into hydration injection opening 583 and is pushed in, opening injection port 588. Vacuum from inside fitment 590 may be used to draw the hydration fluid into pouch 510, illustratively into chambers 592b-592l, for subsequent movement into various blisters of pouch 510. Cannula 675 is removed from hydration injection opening 583, pouch 510 is removed from loading station 600 and placed into instrument 800, and the run started. It is understood that removal of the vials is illustrative only. If the configuration of the instrument and vials permit, the vials may be inserted permanently in the injection ports, thereby becoming part of the closed system of the pouch and minimizing contamination from the sample. In such an embodiment, a seal bar may not be needed.

In the illustrative embodiment of sample vial 650 discussed above, tongue 660 has a volume equal to or greater than the volume of cannula 655. In one exemplary embodiment where the pouch has a fill volume of 1 ml, vial body 654 may be provided with 1.5 ml of sample fluid 652 and volume of 1 ml of air 645 above the sample fluid. Thus, the air is 40% of the volume of the vial body. However, it is understood that other percentages of air may be used, including 10%, 20%, 30% 50%, 60%, 70%, 80%, and amounts in between. When tongue 660 is inserted through opening 657, the air above the sample fluid is compressed, illustratively by about 50%, but compression in the range of 40-60%, 30-70%, 20-80%, and 10-90% are all possible. It is understood that choice of volume of air and sample fluid depends on size of sample, diameter of cannula, whether removal of the vials prior to running the fluidic reaction is desired, and on a number of other factors. For example, scooped or swabbed samples may need a significantly larger volume of sample fluid, regardless of the fill volume of the fluidic system.

Illustrative vial bodies 654 and 674 are cylindrical. However, since these illustrative vials are provided without plungers, it is understood that the vial bodies need not have circular cross-sections, and that any body shape is within the scope of this invention.

Figure 19:
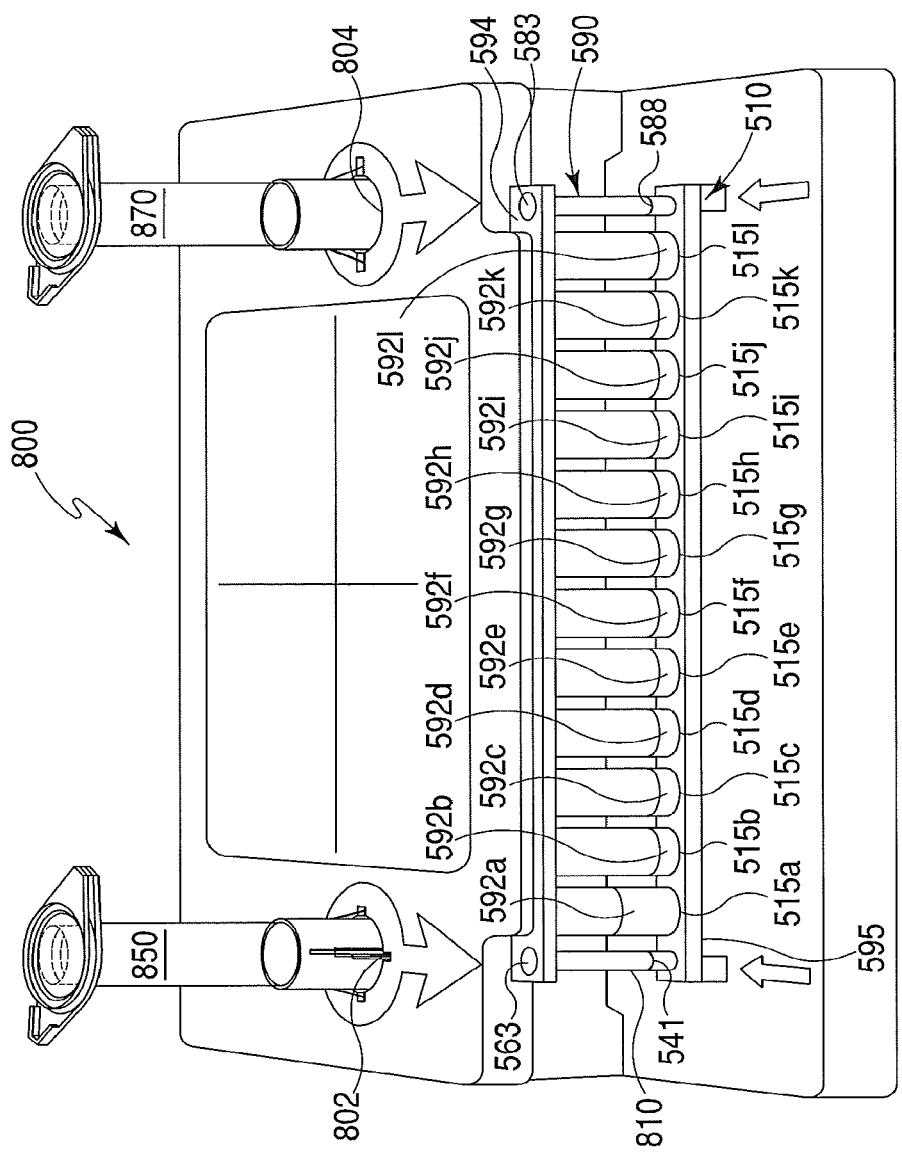
FIG. 19 shows a loading station comparable to FIG. 16, but displaying a different loading station configuration and vials for use with the loading station.

FIGS. 19-21 show an alternative embodiment to loading station 600 and vials 650, 670, with like numbers indicating similar parts. Loading station 800, as shown in FIG. 19, may be similar to loading station 600, with sample vial receptacle 802 and hydration vial receptacle 804, and slot 810 for receiving pouch 510, similar to those shown in FIG. 12. However, according to at least one embodiment, the shape and location of the receptacles are significantly different between loading station 600 and loading station 800. For instance, in at least one embodiment, as compared to receptacles 602, 604 of loading station 600, receptacles 802 and 804 are closer to pouch 510. With this reduced distance, there is less opportunity for drips to occur upon loading pouch 510. Furthermore, as best seen in FIGS. 20-21, bottom cap 864 of sample vial 850 is provided with four relatively short fins 867 that fit within four matching slots 803 of sample vial receptacle 802, and bottom cap 884 of hydration vial 870 is provided with two relatively longer fins 887 that fit within two matching slots 805 of hydration vial receptacle 804. These fins replace the hexagonal portions 666 and 686 of vials 650 and 670. The larger number of fins 867 on bottom cap 864 prevents sample vial 850 from being placed in hydration vial receptacle 804, and the longer fins 887 of bottom cap 884 prevent hydration vial 870 from being placed in sample vial receptacle 802. However, it is understood that the use of fins of different sizes and numbers is illustrative only, and that different keying systems are within the scope of this disclosure. As discussed above with respect to loading station 600, the receptacles 802, 804 of loading station 800 may be used to assist with twisting off bottom caps 684, 884 from their respective vial bodies 854, 874, to aid with the loading process.

While sample vials 650, 850 and hydration vials 670, 870 are used in the illustrative example for loading of pouch 590, it is understood that these loading vials are suitable for loading any of the pouches disclosed herein. They are also suitable for loading other fluidic or microfluidic device, especially fluidic devices that are configured to draw liquid into the fluidic device using vacuum or suction.

REFERENCES

1. Wittwer C T, Fillmore G C, Garling D J. Minimizing the time required for DNA amplification by efficient heat transfer to small samples. Anal Biochem. 1990 May 1; 186(2):328-31.
2. Wittwer C T, Garling D J. Rapid cycle DNA amplification: time and temperature optimization. Biotechniques. 1991 January; 10(1):76-83.
3. Wittwer C T, Herrmann M G, Moss A A, Rasmussen R P. Continuous fluorescence monitoring of rapid cycle DNA amplification. Biotechniques. 1997 January; 22(1):130-1, 134-8.
4. Wittwer C T, Ririe K M, Andrew R V, David D A, Gundry R A, Balis U J. The LightCycler: a microvolume multi-sample fluorimeter with rapid temperature control. Biotechniques. 1997 January; 22(1):176-81
5. Gundry C N, Vandersteen J G, Reed G H, Pryor R J, Chen J, Wittwer C T. Amplicon melting analysis with labeled primers: a closed-tube method for differentiating homozygotes and heterozygotes. Clin Chem. 2003 March; 49(3): 396-406.
6. Wittwer C T, Reed G H, Gundry C N, Vandersteen J G, Pryor R J., High-resolution genotyping by amplicon melting analysis using LCGreen. Clin Chem. 2003 June; 49(6 Pt 1):853-60.
7. McKinney J T, Longo N, Hahn S, Matern D, Rinaldo P, Dobrowolski S F. Comprehensive analysis of the human medium chain acyl-CoA dehydrogenase gene. Mol Gen Metab. In press
8. Dobrowolski S F, Amat di San Filippo C, McKinney J T, Wilcken B, Longo N Identification of novel mutations in the SLC22A5 gene in primary carnitine deficiency with dye-binding/high-resolution thermal denaturation, Human Mutation, submitted
9. McKinney J T, Saunders C, Dobrowolski S F, High-resolution melting analysis of the human galactose-1-phosphate uridyl transferase gene, in preparation
10. http://www.defenselink.mil/contracts/2003/ct20030925.html
11. Poritz M A, Abbott R, Gerber T, Thatcher S, Bird A, Tuck A, Newswander A M, Belisle S, Ririe K, A Handheld, Battery-operated Real-time PCR Machine, American Society for Microbiology Annual Meeting, Baltimore Md., Mar. 9-12, 2003
12. Elnifro E M, Ashshi A M, Cooper R J, Klapper P E. Multiplex PCR: optimization and application in diagnostic virology. Clin Microbiol Rev. 2000 October; 13(4): 559-70. Review.
13. Elnifro E M, Cooper R J, Klapper P E, Yeo A C, Tullo A B. Multiplex polymerase chain reaction for diagnosis of viral and chlamydial keratoconjunctivitis. Invest Ophthalmol Vis Sci. 2000 June; 41(7):1818-22.
14. Giaever, G., et al. Genomic profiling of drug sensitivities via induced haploinsufficiency. Nature Genetics. 1999, 21, 278-283
15. Winzeler, E., et al Functional Characterization of the *Saccharomyces cerevisiae* Genome by Gene Deletion and Parallel Analysis. Science. 1999. 285, 901-906.
16. Sano, T., C. L. Smith, and C. R. Cantor, Immuno-PCR: very sensitive antigen detection by means of specific antibody-DNA conjugates. Science, 1992. 258(5079): p. 120-2.
17. Niemeyer, C. M., M. Adler, and R. Wacker, Immuno-PCR: high sensitivity detection of proteins by nucleic acid amplification. Trends Biotechnol, 2005. 23(4): p. 208-16.
18. Adler, M., Immuno-PCR as a clinical laboratory tool. Adv Clin Chem, 2005. 39: p. 239-92.
19. Barletta, J. M., et al., Detection of ultra-low levels of pathologic prion protein in scrapie infected hamster brain homogenates using real-time immuno-PCR. J Virol Methods, 2005. 127(2): p. 154-64.
20. Adler, M., et al., Detection of Rotavirus from stool samples using a standardized immuno-PCR ("Imperacer") method with end-point and real-time detection. Biochem Biophys Res Commun, 2005. 333(4): p. 1289-94.
21. Lind, K. and M. Kubista, Development and evaluation of three real-time immuno-PCR assemblages for quantification of PSA. J Immunol Methods, 2005. 304(1-2): p. 107-16.
22. Schiavo, S., et al., Comparison of fluorometric detection methods for quantitative polymerase chain reaction (PCR). J Immunoassay Immunochem, 2005. 26(1): p. 1-12.
23. Barletta, J. M., D. C. Edelman, and N. T. Constantine, Lowering the detection limits of HIV-1 viral load using real-time immuno-PCR for HIV-1 p24 antigen. Am J Clin Pathol, 2004. 122(1): p. 20-7.
24. McKie, A., et al., A quantitative immuno-PCR assay for the detection of mumps-specific IgG. J Immunol Methods, 2002. 270(1): p. 135-41.
25. Chao, H. Y., et al., A highly sensitive immuno-polymerase chain reaction assay for *Clostridium botulinum* neurotoxin type A. Toxicon, 2004. 43(1): p. 27-34.
26. Wu, H. C., et al., Detection of *Clostridium botulinum* neurotoxin type A using immuno-PCR. Lett Appl Microbiol, 2001. 32(5): p. 321-5.
27. Liang, H., et al., A highly sensitive immuno-PCR assay for detecting Group A *Streptococcus*. J Immunol Methods, 2003. 279(1-2): p. 101-10.
28. Adler, M., R. Wacker, and C. M. Niemeyer, A real-time immuno-PCR assay for routine ultrasensitive quantification of proteins. Biochem Biophys Res Commun, 2003. 308(2): p. 240-50.
29. Allen, R. C., et al., An immuno-PCR method for detecting *Bacillus thuringiensis* CrylAc toxin. J Immunol Methods, 2006. 308(1-2): p. 109-15.
30. Hendrickson, E. R., et al., High sensitivity multianalyte immunoassay using covalent DNA-labeled antibodies and polymerase chain reaction. Nucleic Acids Res, 1995. 23(3): p. 522-9.
31. Joerger, R. D., et al., Analyte detection with DNA-labeled antibodies and polymerase chain reaction. Clin Chem, 1995. 41(9): p. 1371-7.
32. Hujer, et. al., Multi-drug Resistant *Acinetobacter* spp. Isolates from Military and Civilian Patients Treated at the Walter Reed Army Medical Center: Analysis of Antibiotic Resistance Genes. Antimicrob Agents Chemother. 2006 Sep. 25.
33. Sanchez et al., A multiplex assay with 52 single nucleotide polymorphisms for human identification. Electrophoresis. 2006 v27 p. 1713-24.
34. Zhou et al., Closed-tube genotyping with unlabeled oligonucleotide probes and a saturating DNA dye. Clin Chem. 2004 50 p. 1328-35.

Although the invention has been described in detail with reference to preferred embodiments, variations and modifications exist within the scope and spirit of the invention as described and defined in the following claims.

The invention claimed is:

1. A cannulated vial comprising:
 a vial body having an interior vial volume that is sealed from an outside environment by one or more external walls,
 a cannula extending from a bottom surface of the vial body and having a first end and a second end connected by an outer surface and defining an interior cannula volume, the first end in fluid communication with the interior vial volume, and
 a filter located near the bottom surface of the vial body, the filter configured to filter fluid as the fluid passes into the cannula, wherein the filter has a pore size of sufficient diameter to allow fungal, viral, protozoans, and/or bacterial organisms to pass therethrough into the cannula, but small enough to capture larger particulate matter.

2. The cannulated vial of claim 1, further comprising a removable bottom cap having first end sized and shaped to removably seal the second end of the cannula from the outside environment when the bottom cap is affixed to the second end of the cannula, wherein fluid provided in the interior volume is under pressure, and removal of the bottom cap exposes the second end of the cannula to the outside environment, thereby forcing fluid through the cannula.

3. The cannulated vial of claim 1, the vial body further comprising an opening and a cap having a tongue, wherein the interior volume is pressurized by placement of the tongue through the opening.

4. The cannulated vial of claim 1, wherein the cannulated vial does not contain a plunger.

5. The cannulated vial of claim 1, in combination with a second cannulated vial, the second cannulated vial comprising:
 a vial body having an interior vial volume that is sealed from an outside environment by one or more external walls, and
 a cannula extending from a bottom surface of the vial body and having a first end and a second end connected by an outer surface and defining an interior cannula volume, the first end in fluid communication with the interior vial volume, and
 wherein the second cannulated vial does not contain a plunger.

6. The cannulated vial of claim 5, wherein the second cannulated vial does not include a filter.

7. The cannulated vial of claim 5, wherein the second cannulated vial further comprises a removable bottom cap having first end sized and shaped to removably seal the second end of the cannula from the outside environment when the bottom cap is affixed to the second end of the cannula, wherein fluid provided in the interior volume is under pressure, and removal of the bottom cap exposes the second end of the cannula to the outside environment, thereby forcing fluid through the cannula.

8. A cannulated vial comprising:
 a vial body having a top surface at one end, a bottom surface at an opposite end, and an exterior wall therebetween defining an interior vial volume, the top surface having an opening,
 a cannula extending from the bottom surface and having a first end, a second end, and an outer surface therebetween defining a cannula volume, the first end in fluid communication with the interior vial volume, and
 a cap having a tongue, the tongue sized to sealably close the opening of the top surface, the tongue further having a volume greater than or equal to the cannula volume.

9. The cannulated vial of claim 8, further comprising a removable bottom cap sized and shaped to operably seal the second end of the cannula from an outside environment.

10. The cannulated vial of claim 9, wherein placing the tongue into the opening of the top surface to sealably close the opening pressurizes the interior vial volume, and removal of the bottom cap causes pressurized fluid to be forced into the cannula.

11. The cannulated vial of claim 10, wherein the tongue volume is greater than the cannula volume, and removal of the bottom cap allows fluid to emit from of the cannula.

12. The cannulated vial of claim 10, wherein the vial body further contains a volume of air and the tongue has a volume sufficient to compress the air by 20-80%.

13. The cannulated vial of claim 12, wherein the tongue has a volume sufficient to compress the air by 50%.

14. The cannulated vial of claim 11, wherein the bottom cap is configured to capture the emitted fluid.

15. The cannulated vial of claim 8, further comprising a filter located near the bottom surface of the vial body, the filter configured to filter fluid as the fluid passes into the cannula.

16. The cannulated vial of claim 15, wherein the filter has a pore size of sufficient diameter to allow fungal, viral, protozoans, and/or bacterial organisms to pass therethrough into the cannula, but small enough to capture larger particulate matter.

17. The cannulated vial of claim 15, wherein the cannulated vial does not contain a plunger.

18. A cannulated vial comprising:
 a vial body having an interior volume sealed from an outside environment, the interior volume comprising a fluid;
 a cannula extending away from a bottom surface of the vial body, said cannula having a first end and a second end, the first end of the cannula adjacent to the bottom surface of the vial body and the second end of the cannula sealed from the outside environment, wherein the cannula does not extend into the fluid in the vial body; and
 a filter located near the bottom surface of the vial body configured to filter fluid prior to entering the cannula, wherein the filter has a pore size of sufficient diameter to allow fungal, viral, protozoans, and/or bacterial organisms to pass therethrough into the cannula, but small enough to capture larger particulate matter.

19. The cannulated vial of claim 18 in combination with a fluidic system, the fluidic system including a first port configured for engagement with the second end of the cannula, wherein the first port of the fluidic system is provided under an amount of vacuum so as to draw a volume of fluid out of the vial body through the cannula into the fluidic system.

20. The cannulated vial of claim 18 in combination with a second cannulated vial, the second cannulated vial comprising:
- a vial body having an interior vial volume that is sealed from an outside environment by one or more external walls, and
- a cannula extending from a bottom surface of the vial body and having a first end and a second end connected by an outer surface and defining an interior cannula volume, the first end in fluid communication with the interior vial volume,
- wherein the second cannulated vial does not contain a plunger and is not provided with the plunger, and
- wherein the second cannulated vial does not include a filter.

* * * * *

UNITED STATES PATENT AND TRADEMARK OFFICE
CERTIFICATE OF CORRECTION

Page 1 of 1

PATENT NO. : 10,913,060 B2
APPLICATION NO. : 16/580749
DATED : February 9, 2021
INVENTOR(S) : Jones et al.

It is certified that error appears in the above-identified patent and that said Letters Patent is hereby corrected as shown below:

On the Title Page

(56) References Cited, U.S. PATENT DOCUMENTS, Page 2, Column 1, Line 66:
Please correct "2010/0055383" to read -- 2010/0056383 --

(56) References Cited, OTHER PUBLICATIONS, Page 2, Column 2, Line 35, Elniero cite:
Please correct "Elniero" to read -- Elnifro --

(56) References Cited, OTHER PUBLICATIONS, Page 2, Column 2, Line 37, Elniero cite:
Please correct "41:1816-1822" to read -- 41:1818-1822 --

(56) References Cited, OTHER PUBLICATIONS, Page 2, Column 2, Line 42, Guncry cite:
Please correct "Guncry" to read -- Gundry --

(56) References Cited, OTHER PUBLICATIONS, Page 2, Column 2, Line 53:
Please correct "PCT/US2012/084286" to read -- PCT/US2012/064286 --

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*